(12) United States Patent
Pederson et al.

(10) Patent No.: US 11,247,076 B2
(45) Date of Patent: *Feb. 15, 2022

(54) TISSUE NECROSIS METHODS AND APPARATUS

(71) Applicant: Auris Health, Inc., Redwood City, CA (US)

(72) Inventors: Michael J. Pederson, Minneapolis, MN (US); Patrick J. Phillips, Los Altos, CA (US); John P. Madden, Emerald Hills, CA (US); Michael J. Horzewski, San Jose, CA (US)

(73) Assignee: Auris Health, Inc., Redwood City, CA (US)

( * ) Notice: Subject to any disclaimer, the term of this patent is extended or adjusted under 35 U.S.C. 154(b) by 289 days.

This patent is subject to a terminal disclaimer.

(21) Appl. No.: 16/367,458

(22) Filed: Mar. 28, 2019

(65) Prior Publication Data

US 2019/0232092 A1    Aug. 1, 2019

Related U.S. Application Data

(63) Continuation of application No. 13/754,268, filed on Jan. 30, 2013, now Pat. No. 10,286,231.
(Continued)

(51) Int. Cl.
*A61N 7/02* (2006.01)
*A61B 17/22* (2006.01)
(Continued)

(52) U.S. Cl.
CPC ............ *A61N 7/02* (2013.01); *A61B 17/2202* (2013.01); *A61N 7/022* (2013.01);
(Continued)

(58) Field of Classification Search
CPC ............ A61B 17/2202; A61B 17/3478; A61B 2017/22021; A61B 2018/00011;
(Continued)

(56) References Cited

U.S. PATENT DOCUMENTS

| 3,638,973 A | 2/1972 | Charles |
| 5,295,484 A | 3/1994 | Marcus et al. |

(Continued)

FOREIGN PATENT DOCUMENTS

| CN | 1787790 A | 6/2006 |
| EP | 1498072 A1 | 1/2005 |

(Continued)

OTHER PUBLICATIONS

European search report and search opinion dated Oct. 14, 2015 for EP Application No. 13744162.2.
(Continued)

*Primary Examiner* — Khadijeh A Vahdat
(74) *Attorney, Agent, or Firm* — Chang & Hale LLP

(57) ABSTRACT

Apparatus and methods for creating tissue necrosis include an energy delivery apparatus that can be positioned adjacent a target treatment site such as a vessel without direct contact with the treatment site tissue. Collimated energy is then directed to the vessel to create necrotic regions in the tissue. Exemplary use in renal vessels creates necrotic regions in adjacent nerves which can alleviate hypertension in a patient.

19 Claims, 25 Drawing Sheets

Related U.S. Application Data

(60) Provisional application No. 61/592,392, filed on Jan. 30, 2012.

(51) Int. Cl.
 *A61N 7/00* (2006.01)
 *A61B 17/34* (2006.01)
 *A61B 18/00* (2006.01)

(52) U.S. Cl.
 CPC . *A61B 17/3478* (2013.01); *A61B 2017/22021* (2013.01); *A61B 2018/00011* (2013.01); *A61B 2018/00404* (2013.01); *A61B 2018/00434* (2013.01); *A61B 2018/00511* (2013.01); *A61B 2018/00577* (2013.01); *A61N 2007/0043* (2013.01); *A61N 2007/0052* (2013.01); *A61N 2007/0069* (2013.01); *A61N 2007/0078* (2013.01); *A61N 2007/0091* (2013.01); *A61N 2007/0095* (2013.01)

(58) Field of Classification Search
 CPC A61B 2018/00404; A61B 2018/00434; A61B 2018/00511; A61B 2018/00577; A61N 2007/0043; A61N 2007/0052; A61N 2007/0069; A61N 2007/0091; A61N 2007/0095; A61N 7/02; A61N 7/022
 USPC .............................. 606/51–52, 169, 205–207
 See application file for complete search history.

(56) References Cited

U.S. PATENT DOCUMENTS

| | | | |
|---|---|---|---|
| 5,342,292 | A | 8/1994 | Nita et al. |
| 6,012,457 | A | 1/2000 | Lesh |
| 6,024,740 | A | 2/2000 | Lesh et al. |
| 6,052,576 | A | 4/2000 | Lambourg |
| 6,117,101 | A | 9/2000 | Diederich et al. |
| 6,164,283 | A | 12/2000 | Lesh |
| 6,245,064 | B1 | 6/2001 | Lesh et al. |
| 6,254,599 | B1 | 7/2001 | Lesh et al. |
| 6,305,378 | B1 | 10/2001 | Lesh |
| 6,383,151 | B1 | 5/2002 | Diederich et al. |
| 6,416,511 | B1 | 7/2002 | Lesh et al. |
| 6,514,249 | B1 | 2/2003 | Maguire et al. |
| 6,547,788 | B1 | 4/2003 | Maguire et al. |
| 6,605,084 | B2 | 8/2003 | Acker et al. |
| 6,635,054 | B2 | 10/2003 | Fjield et al. |
| 6,652,515 | B1 | 11/2003 | Maguire et al. |
| 6,780,183 | B2 | 8/2004 | Jimenez et al. |
| 6,872,205 | B2 | 3/2005 | Lesh et al. |
| 6,953,460 | B2 | 10/2005 | Maguire et al. |
| 6,954,977 | B2 | 10/2005 | Maguire et al. |
| 6,955,173 | B2 | 10/2005 | Lesh |
| 6,964,660 | B2 | 11/2005 | Maguire et al. |
| 6,966,908 | B2 | 11/2005 | Maguire et al. |
| 6,978,174 | B2 | 12/2005 | Gelfand et al. |
| 6,997,925 | B2 | 2/2006 | Maguire et al. |
| 7,162,303 | B2 | 1/2007 | Levin et al. |
| 7,306,593 | B2 | 12/2007 | Keidar et al. |
| 7,308,593 | B2 | 12/2007 | Jacobson et al. |
| 7,617,005 | B2 | 11/2009 | Demarais et al. |
| 7,647,115 | B2 | 1/2010 | Levin et al. |
| 7,653,438 | B2 | 1/2010 | Deem et al. |
| 7,717,948 | B2 | 5/2010 | Demarais et al. |
| 7,756,583 | B2 | 7/2010 | Demarais et al. |
| 7,853,333 | B2 | 12/2010 | Demarais |
| 7,873,417 | B2 | 1/2011 | Demarais et al. |
| 7,937,143 | B2 | 5/2011 | Demarais et al. |
| 10,286,231 | B2 | 5/2019 | Pederson |
| 2002/0087156 | A1 | 7/2002 | Maguire et al. |
| 2004/0087936 | A1 | 5/2004 | Stern et al. |
| 2005/0015079 | A1 | 1/2005 | Keider et al. |
| 2005/0234523 | A1 | 10/2005 | Levin et al. |
| 2005/0267453 | A1 | 12/2005 | Wong et al. |
| 2006/0025756 | A1 | 2/2006 | Francischelli et al. |
| 2006/0025821 | A1 | 2/2006 | Gelfand et al. |
| 2006/0041277 | A1 | 2/2006 | Deem et al. |
| 2006/0212076 | A1 | 9/2006 | Demarais et al. |
| 2006/0212078 | A1 | 9/2006 | Demarais et al. |
| 2006/0265014 | A1 | 11/2006 | Demarais et al. |
| 2006/0265015 | A1 | 11/2006 | Demarais et al. |
| 2006/0271111 | A1 | 11/2006 | Demarais et al. |
| 2006/0276852 | A1 | 12/2006 | Demarais et al. |
| 2007/0129720 | A1 | 6/2007 | Demarais et al. |
| 2007/0173899 | A1 | 7/2007 | Levin et al. |
| 2007/0260295 | A1 | 11/2007 | Chen et al. |
| 2007/0265687 | A1 | 11/2007 | Deem et al. |
| 2008/0213331 | A1 | 9/2008 | Gelfand et al. |
| 2008/0255642 | A1 | 10/2008 | Zarins et al. |
| 2009/0036948 | A1 | 2/2009 | Levin et al. |
| 2009/0062873 | A1 | 3/2009 | Wu et al. |
| 2009/0076409 | A1 | 3/2009 | Wu et al. |
| 2010/0010567 | A1 | 1/2010 | Deem et al. |
| 2010/0016762 | A1 | 1/2010 | Thapliyal et al. |
| 2010/0113928 | A1 | 5/2010 | Thapliyal et al. |
| 2010/0137860 | A1 | 6/2010 | Demarais et al. |
| 2010/0137952 | A1 | 6/2010 | Demarais et al. |
| 2010/0168572 | A1 | 7/2010 | Sliwa et al. |
| 2010/0168731 | A1 | 7/2010 | Wu et al. |
| 2010/0168739 | A1 | 7/2010 | Wu et al. |
| 2010/0174282 | A1 | 7/2010 | Demarais et al. |
| 2010/0191112 | A1 | 7/2010 | Demarais et al. |
| 2010/0222851 | A1 | 9/2010 | Deem et al. |
| 2010/0222854 | A1 | 9/2010 | Demarais et al. |
| 2010/0249773 | A1 | 9/2010 | Clark et al. |
| 2010/0268307 | A1 | 10/2010 | Demarais et al. |
| 2011/0028886 | A1 | 2/2011 | Mon |
| 2011/0060324 | A1 | 3/2011 | Wu et al. |
| 2011/0092880 | A1 | 4/2011 | Gertner |
| 2011/0112400 | A1 | 5/2011 | Emery et al. |
| 2011/0166499 | A1 | 7/2011 | Demarais et al. |
| 2011/0178570 | A1 | 7/2011 | Demarais |
| 2011/0200171 | A1 | 8/2011 | Beetel et al. |
| 2011/0202098 | A1 | 8/2011 | Demarais et al. |
| 2011/0208096 | A1 | 8/2011 | Demarais et al. |
| 2011/0257523 | A1 | 10/2011 | Hastings et al. |
| 2011/0257563 | A1 | 10/2011 | Thapliyal et al. |
| 2011/0257564 | A1 | 10/2011 | Demarais et al. |
| 2011/0264011 | A1 | 10/2011 | Wu et al. |
| 2011/0264075 | A1 | 10/2011 | Leung et al. |
| 2012/0059286 | A1 | 3/2012 | Hastings et al. |
| 2012/0265192 | A1 | 10/2012 | Sliwa et al. |
| 2013/0110145 | A1 | 5/2013 | Weitzman |
| 2013/0158537 | A1 | 6/2013 | Deladi et al. |

FOREIGN PATENT DOCUMENTS

| | | |
|---|---|---|
| WO | WO-9902096 A1 | 1/1999 |
| WO | WO-2005117734 A2 | 12/2005 |
| WO | WO-2005117734 A3 | 12/2006 |
| WO | WO-2007134258 A2 | 11/2007 |
| WO | WO-2011053757 A1 | 5/2011 |
| WO | WO-2011056514 A1 | 5/2011 |

OTHER PUBLICATIONS

International search report and written opinion dated May 13, 2013 for PCT/US2013/023915.
Office action dated Jan. 20, 2016 for U.S. Appl. No. 13/754,268.
Office action dated Apr. 10, 2015 for U.S. Appl. No. 13/754,268.
Office Action dated Apr. 26, 2017 for U.S. Appl. No. 13/754,268.
Office Action dated Nov. 3, 2017 for U.S. Appl. No. 13/754,268.

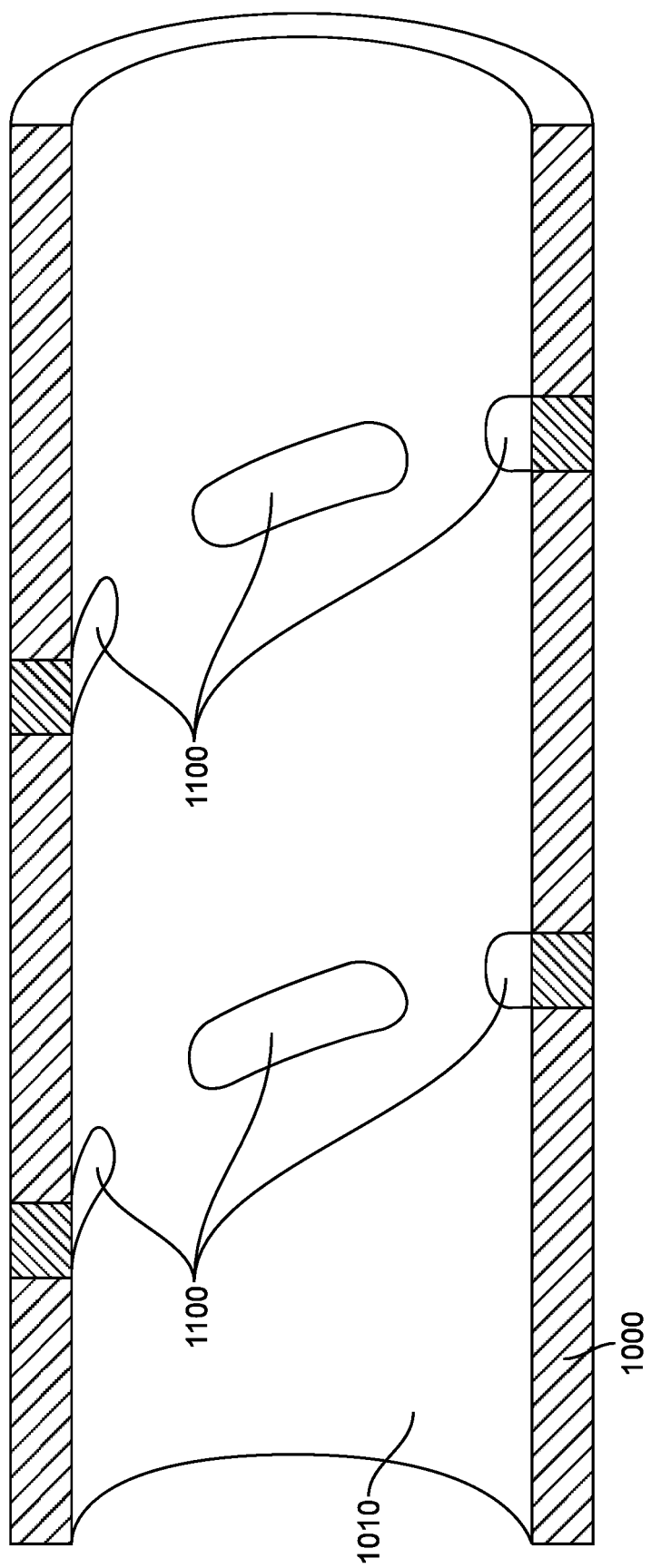

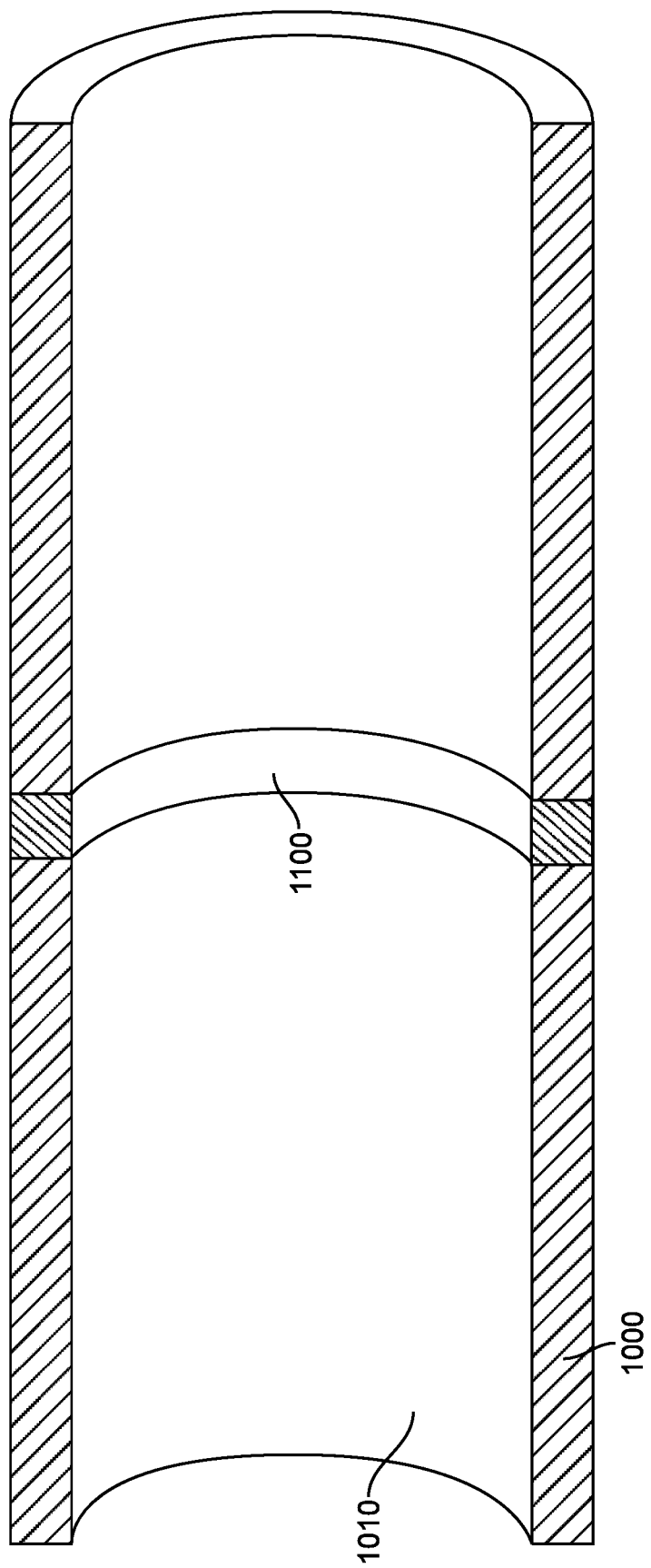

TISSUE NECROSIS METHODS AND APPARATUS

CROSS-REFERENCE

This application is a continuation of U.S. patent application Ser. No. 13/754,268, now U.S. Pat. No. 10,286,231, filed Jan. 30, 2013, which claims the benefit of priority of Provisional U.S. Patent Application Ser. No. 61/592,392, filed on Jan. 30, 2012, which is fully incorporated by reference herein for all purposes.

This application is related to the following U.S. Pat. Nos. 7,950,397; 7,942,871; and also related to the following U.S. patent application Ser. Nos. 13/092,747; 12/480,929; 12/480,256; 12/483,174; 12/482,640; 12/505,326; 12/505,335; 12/620,287; 12/695,857; 12/609,759; 12/609,274; 12/609,705; 12/909,642; and also related to U.S. Provisional Patent Application No. 61/475,130; the entire contents of each of which is incorporated herein by reference.

BACKGROUND OF THE INVENTION

1. Field of the Invention

The present invention describes methods and apparatus for creating tissue necrosis. More specifically, this invention pertains to the creation of necrotic tissue having the effect of blocking conductive pathways. This invention may be used in the treatment of hypertension, cardiac, neurologic, renal, and various other disorders.

Hypertension affects an estimated one billion patients worldwide. The kidney is directly involved in body fluid homeostasis, and its ability to excrete sodium chloride and maintain sodium balance, extracellular fluid volume, and blood volume are major factors in the regulation of long-term arterial pressure. Both the kidneys and the autonomic nervous system contribute to kidney function, with the two being linked through the renal nerves.

The renal sympathetic nerves play a significant role in the pathophysiology of hypertension, where increased stimulation of these nerves triggers changes in renal vascular resistance, renin release, and retention of water and sodium. The afferent renal nerves monitor pressure changes in the kidney and relay the information to the central nervous system which then influences function of effector organs. Renal receptors influence cardiovascular function via increased activity of the sympathetic nerves to the kidney and other vascular beds and organs. The increase in sympathetic nerve activity and the activation of afferent renal nerves directly contributes to hypertension.

Untreated, hypertension can lead or contribute to cardiovascular (e.g. myocardial infarction, congestive heart failure), neurologic (e.g. stroke, dementia), and renal (e.g. chronic renal failure) disorders all having a direct effect on morbidity and mortality. Current therapies for hypertension primarily consist of lifestyle changes and pharmacological therapy, with varying degrees of success. In a subset of these patients with persistent hypertension, interventional therapy has been tested.

Initial treatment for hypertension is a change in lifestyle, including: diet, exercise, and weight loss, as well as elimination of smoking. Dietary modifications include limiting sodium intake, and consumption of nuts, whole grains, fish, poultry, fruits, and vegetables. In addition, a decrease in the consumption of red meats, sweets, and sugar is recommended. Exercise, weight loss, and non-smoking all contribute to improved cardiovascular function and decreased cardiac demand.

Pharmacologic approaches consist of individual or combinations of antihypertensive drugs, namely: diuretics, which reduce blood volume by eliminating sodium and water; beta blockers, which reduce cardiac workload and dilate blood vessels; angiotensin-converting enzyme inhibitors; Angiotensin II receptor blockers; and calcium channels blockers, all of which dilate blood vessels and may reduce heart rate; and renin inhibitors which decrease the production of renin, an enzyme in the chain that increases blood pressure. In addition to these medications, in certain cases these drugs are administered: alpha blockers, to reduce vasoconstrictive chemicals; alpha-beta blockers, which also reduce cardiac output; central nervous system agents to reduce vasoconstriction; and vasodilators, used to increase vessel diameter and reduce pressure. Combinations of all these medications are administered in light of their different effects on patients of varying race, gender, and age.

Patients taking multiple simultaneous medications without relief of hypertension are considered to have resistant hypertension. In the case of resistant hypertension, an invasive approach wherein the functionality of the renal nerves or sympathetic nervous elements is decreased or eliminated is proposed. This approach may also be applicable as a therapy for controlled hypertension.

While existing therapies may have demonstrated a limited effect in treating these disorders, improved systems and methods for creating necrotic tissue and effecting nerve activity are needed. Furthermore, it would be desirable for such systems to have an increased control in, for example: position, profile, and morphology of the generated necrotic tissue, while also offering greater patient safety and ultimately greater efficacy.

2. Background Art

Other devices based on ultrasound energy to create lesions are described in U.S. Pat. Nos. 6,997,925; 6,966,908; 6,964,660; 6,954,977; 6,953,460; 6,652,515; 6,547,788; and 6,514,249 to Maguire et al.; U.S. Pat. Nos. 6,955,173; 6,052,576; 6,305,378; 6,164,283; and 6,012,457 to Lesh; U.S. Pat. Nos. 6,872,205; 6,416,511; 6,254,599; 6,245,064; and 6,024,740; to Lesh et al.; 6,383,151; 6,117,101; and WO 99/02096 to Diederich et al.; U.S. Pat. No. 6,635,054 to Fjield et al.; U.S. Pat. No. 6,780,183 to Jimenez et al.; U.S. Pat. No. 6,605,084 to Acker et al.; U.S. Pat. No. 5,295,484 to Marcus et al.; and WO 2005/117734 to Wong et al. Other related patents and patent publications include: U.S. Pat. Nos. 6,978,174; 7,162,303; 7,617,005; 7,620,451; 7,647,115; 7,653,438; 7,717,948; 7,756,583; 7,853,333; 7,873,417; 7,937,143; US20060212078; US20070173899; US20100137952; US20110060324; US20060212076; US20070265687; US20100168731; US20110112400; US20060265014; US20080213331; US20100168739; US20110166499; US20060265015; US20080255642; US20100174282; US20110178570; US20060271111; US20090036948; US20100191112; US20110200171; US20060276852; US20090062873; US20100222851; US20110202098; US20060025821; US20090076409; US20100222854; US20110208096; US20070129720; US20100137860; US20100249773; US20110257564; US20050234523; US20060041277; US20100268307; US20110264011; US20100010567; US20110264075.

SUMMARY OF THE INVENTION

The present invention provides medical systems and methods to create tissue necrosis, and more specifically to medical systems and methods used to deliver energy to tissue in the treatment of hypertension, cardiac, neurologic, renal, and other medical conditions.

One aspect of the invention pertains to a method for creating tissue necrosis, the method comprising the steps of: providing a catheter that carries an energy delivery apparatus, positioning the energy delivery apparatus adjacent a vessel without contact therebetween, delivering collimated energy from the energy delivery apparatus to the vessel, and creating sufficient damage to the tissue with the collimated energy to cause tissue necrosis. In some embodiments of the invention delivering collimated energy comprises delivering ultrasound energy. Some embodiments may also include the step of cooling the energy delivery apparatus.

Additionally, some embodiments of the invention comprise irrigating the energy delivery apparatus with a fluid.

In some embodiments, creating sufficient damage may comprise creating one or more linear tissue necrosis regions. The one or more linear necrosis regions may further comprise lesions selected from the group consisting of arc, spiral, helix, straight, dashed, freeform line, or variations or combinations thereof.

In some embodiments causing tissue necrosis is conducted at least in part by semi-automated control. Causing tissue necrosis may also be conducted at least in part by automated control.

In some embodiments delivering collimated energy comprises delivering the energy to the tissue in a substantially radial direction. In some embodiments, delivering collimated energy comprises delivering the energy to the tissue in a substantially longitudinal direction.

Some embodiments of invention feature a controller which controls the energy delivery.

The method of creating tissue necrosis may further comprise deflecting a shaft of the catheter thereby facilitating positioning of the catheter at a target location. Some embodiments further comprise sensing or measuring a position and/or an orientation of an element of the catheter, and adjusting a control feature in response to the sensed or measured information obtained.

Some embodiments of the invention also comprise the step of delivering energy to the tissue in order to determine information pertaining to one or more of the following: tissue structures, morphology, physiology, nerves, calcified regions, vessel wall thickness, distance from the energy delivery apparatus to a structure, and progression of lesion formation. Such embodiments may further comprise adjusting parameters of the energy delivered and/or adjusting movement of an element of the catheter in response to the information received.

Some embodiment also comprise the step of delivering a pain reduction medicament. The delivered energy mentioned above may also enhance delivery of the pain reduction medicament to a tissue through one or more of the following: acoustic pressure or streaming, sonoporation, bursting or altering encapsulated drug delivery vehicles, or thermal stimulation.

In exemplary embodiments of the invention the vessel comprises a renal vessel, and tissue necrosis comprises necrosis of a nerve. Necrosis of the nerve may alleviate hypertension in a patient.

Another embodiment of the method for creating tissue necrosis comprises: directing an energy delivery apparatus percutaneously to a target vessel, positioning the energy delivery apparatus in a desired location within the target vessel, initiating energy delivery, and moving the energy delivery apparatus while deliverying energy to create a desired region of tissue necrosis.

Some embodiments of the invention further comprise turning power on and off to the energy delivery apparatus while moving the energy delivery apparatus or in between movement of the energy delivery apparatus.

Some embodiments of the invention further comprise imaging during or interleaved with the creation of tissue necrosis.

Another aspect of the present invention entails, a system for creating necrotic tissue in a patient comprising a catheter (also referred to as energy delivery catheter) suitable for delivering energy sufficient to create tissue necrosis. The catheter may be constructed to enable radial and/or longitudinal movement of the energy delivery apparatus with respect to other components or structures of the catheter, or other devices (e.g. sheath or guiding catheter). The energy delivery apparatus comprising one or more elements capable of delivering and/or receiving energy, such as one or more ultrasound transducers. The catheter may be connected to a component (e.g. controller and/or generator) which receives and/or sends information from/to the catheter and/or has some level of control over functions of the catheter. The catheter may have one or more deflectable sections in the distal region of the catheter, the deflectable section(s) being delectable in one or more than one plane. The deflectable sections may be on the same shaft or on relatively independent shafts (e.g. coaxial shafts).

In another aspect of the present invention, movement of the deflecting section or sections may be facilitated by pull and/or push element or elements (e.g. wires, fibers, combinations thereof, etc.) This element or elements may function with a supporting element or elements (e.g. surrounded at least in part by a coil or element with fixed or varying compressive strength). In addition, the supporting element or elements may be stationary, movable, or capable of being temporarily or permanently fixed in a given position.

In another aspect of the present invention, the energy delivery apparatus may be for example; side-, distal-, and/or radial-firing. The energy may be direct or reflected to the target tissue.

In another aspect of the present invention, components or elements of the catheter may be straight, preshaped, or deflectable to one or more desired configurations.

In another aspect of the present invention, the catheter may be configured to be used over a guide wire or have an integral guide wire or guide member.

In another aspect of the present invention, the catheter may have an atraumatic distal region or tip.

In another aspect of the present invention, a handle may be connected to the catheter which enhances manipulation of the catheter. The handle may have a drive mechanism or mechanisms for movement of the energy delivery apparatus with respect to other components or structures of the catheter, or other devices. The handle may provide feedback or receive information from the controller and or generator and/or catheter.

In another aspect of the present invention, the generator and controller may be combined in an integrated unit.

In another aspect of the present invention, the generator and/or controller may be integrated with the handle.

In another aspect of the present invention, movement and/or actuation of the energy delivery apparatus may be at least in part controlled by the controller and/or generator. These movements may be for example: pre-programmed, auto or semi-automated, input manually, or any combination thereof.

In another aspect of the present invention, the catheter and/or component and/or components which receives and/or sends information from/to the catheter and/or has some level of control over functions of the catheter may provide the ability to determine or limit use of the catheter or component or components.

In another aspect of the present invention, the energy delivered to create the necrotic tissue may be ultrasound.

In another aspect of the present invention, the energy delivered to create the necrotic tissue may be ultrasound in a relatively collimated beam. This energy may be delivered from one or more ultrasound elements.

In another aspect of the present invention, the energy delivery apparatus may be positioned within a structure. The structure may be designed to maintain a blood barrier of fluid between a certain component(s) and/or element(s).

In another aspect of the present invention, the energy delivery apparatus may be directly or indirectly cooled. The effect of cooling the element of elements may aide in the overall performance of the system, including but not limited to efficiency, safety, and therapeutic effect.

In another aspect of the present invention, the energy delivery apparatus may be not in contact with the target tissue during energy delivery.

In another aspect of the present invention, the energy may be delivered to create greater tissue necrosis within the target tissue than at the surface of the target tissue.

In another aspect of the present invention, the energy may be delivered to form tissue necrosis in various shapes, including but not limited to individual or combinations of continuous and/or intermittent lines (e.g. open, closed, crossing, etc), shapes, spots, patterns (e.g. spiral, helix, dashed lines, etc). Any of these may be created by computer and/or mechanical control and/or assist and/or by or with or without operator input.

In another aspect of the present invention, the catheter may be designed to provide acoustic pressure induced flow (e.g. blood, cooling fluid, etc) in the region of energy delivery. The induced flow may remove heat from the surface of the target tissue allowing less or no damage at the tissue surface, preserving the endothelium and/or intimal layer and increasing safety (reduction in thrombus, charring, stenosis, etc.)

In another aspect of the present invention, an element or elements of the system may be used for imaging and/or analysis of tissue. This element or elements may be the same or different from the element or elements used to deliver energy to create necrotic tissue. Information from the element or elements may be used to determine distance from the element to a structure, to gather information about the structure or structures (e.g. thickness, morphology, physiology, multiple structures, structure recognition, calcified tissue, nerve location and depth, etc.), and other uses. In addition, the information gathered may be used to affect the energy delivered, including but not limited to intensity, duration, power, frequency, speed, etc, as well position of energy delivery. Examples include measuring wall thickness to determine energy dose parameters and identifying structures to determine energy delivery position and intensity. The structure in the region of the energy delivery apparatus (e.g. ultrasound transducer or transducers) may be constructed to improve the signal to noise ratio of the system. In addition, software may be used in or by the system to improve the signal to noise ratio.

In another aspect of the invention, the energy delivery apparatus may be composed of a one- or multi-dimensional array of elements.

In another aspect of the present invention, the imaging and/or therapeutic information may be wholly or partly used in a display image (e.g. 2 dimensional, 3 dimensional, layered, integrated) that may be static, dynamic, interactive, etc.

In another aspect of the present invention, the catheter and/or system may be constructed as to be visualized and/or recognized by and/or interface with additional equipment, including but not limited to fluoroscopy, pumps (e.g. fluid), anatomical mapping, respiration, computed tomography, magnetic resonance imaging, etc.

In another aspect of the invention the catheter, may comprise one or more elements to accommodate varying degrees of stiffness. For instance a proximal segment of the catheter may be relatively stiffer when compared to a distal portion of a catheter.

In another aspect of the invention, the catheter may be sized to pass through a guiding sheath or guiding catheter. The catheter of this or any other embodiment of the invention may comprise an inner shaft and an outer shaft, wherein the inner shaft is translatable and/or rotatable with respect to the outer shaft. When used with a guiding catheter, the guiding catheter (or sheath) may be selectively clamped or tightened down on the outer shaft of the catheter used for energy delivery. This leaves the inner shaft slidable and/or rotatable with respect to the outer shaft and guiding catheter. The inner shaft may then used to guide the energy delivery element. The inner shaft may comprise one or more elements to accommodate varying degrees of stiffness. For example, the inner shaft may be constructed to be stiffer in its proximal portions relative to its distal portions. Such elements may comprise coils, springs, support members, or sections of varying materials and geometries aimed towards altering local stiffness.

In another aspect of the present invention, the catheter has the ability to affect a decrease in the pain associated with delivery of energy and/or creating tissue necrosis, especially necrosis of nerves. This may be accomplished for example, by localized drug delivery through or around the catheter. A suitable pain reduction medicament may be combined with the cooling fluid and delivered directly to the region of energy delivery. Additionally, an agent may be delivered via a component or components on, within, about, and/or passed through the catheter (e.g. port, needle(s), retractable needle(s), etc) to affect the nerves and/or surrounding tissue and decrease the pain of creating tissue necrosis. Further, the ultrasound may also be used to stimulate the drug delivery through sonoporation, bursting or altering encapsulated drug delivery vehicles, and/or thermal stimulated drug delivery.

Descriptions of the embodiments presented herein are understood to be non-limiting. It is understood that features and elements described in the different embodiments above and below may combined with each other.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 7A-D show cross-sections of vessels with representative shapes of necrotic tissue in embodiments of the invention.

DETAILED DESCRIPTION OF THE INVENTION

Figure 1A:
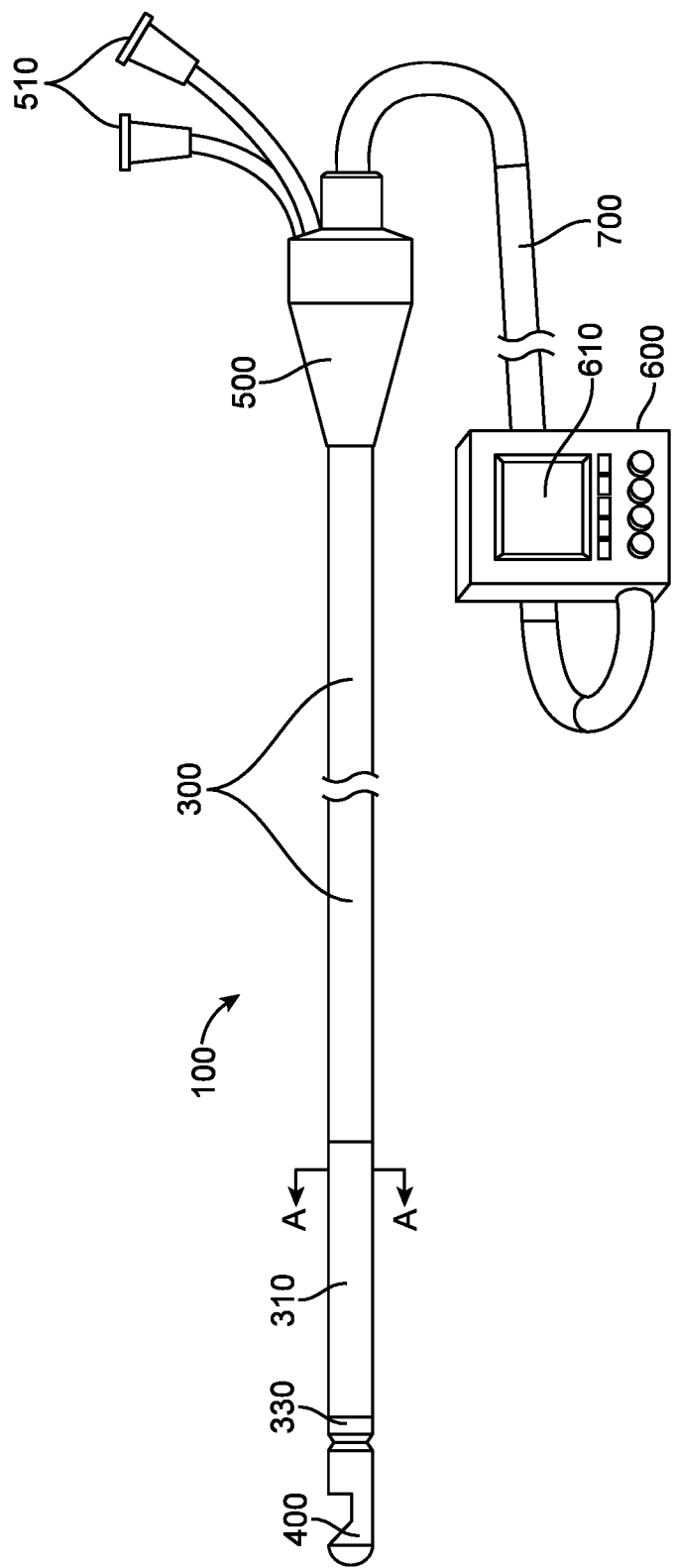
FIGS. 1A-C show side views of a catheter and handle including a controller in embodiments of the invention.

The invention described herein describes a system and methods for creating tissue necrosis. The catheter 100 of the invention includes an elongate member 200. The elongate member includes a distal assembly 400 encompassing an energy delivery apparatus and supporting structure for directing energy to tissue. Uses of the invention include but are not limited to creating tissue necrosis, and more specifically for the treatment hypertension, cardiac, neurologic, renal, and various other disorders.

One aspect of a first embodiment of the invention is shown in FIGS. 1A-D. As shown, the catheter 100 includes an elongate member 200, a longitudinal shaft component or outer shaft 300, a distal assembly 400, and a handle 500. In other implementations, the elongate member 200 and/or outer shaft 300 can be a cannula, tube, or other elongate structure having one or more lumens. The elongate member 200 and/or outer shaft 300 can be made of a flexible tube. Also shown is a handle 400 in the proximal region of the elongate member 200 and outer shaft 300. The elongate member 200 and/or outer shaft 300 and/or handle 500 may be connected to a component (e.g. controller 600) which receives and/or sends information from/to the catheter 100 and/or has some level of control over functions of the catheter 100. Connection of the catheter 100 to the controller 600 may include a connector 700 which may include but is not limited to electrical, optical, mechanical, hydraulic, wireless, and combinations thereof. The handle may also incorporate all the functions of the controller in effect serving as an integral controller handle.

The distal assembly 400 can house an energy delivery apparatus 410, for example, one or more ultrasound transducers (described in more detail in FIGS. 2A-F, 4, 5, 8, 9, and 10) and be connected to the distal region of the elongated member 200.

Although the system described herein includes a distal assembly 400 having an ultrasound transducer as a source of energy, it is envisioned than any of a number of energy sources can be used with various implementations of the invention. Suitable sources of energy include but are not limited to, radio frequency (RF) energy, microwaves, photonic energy, and thermal energy. It is envisioned that the energy source to create necrotic tissue could alternatively be achieved using cooled fluids (e.g., cryogenic fluid). Additionally, although use of a single ultrasound transducer is described herein as an exemplary energy delivery source, it is envisioned that a plurality of energy delivery structures can be included in the distal assembly 400 and that the energy may be delivered in a direct and/or reflected and/or refracted manner.

Figure 1B:
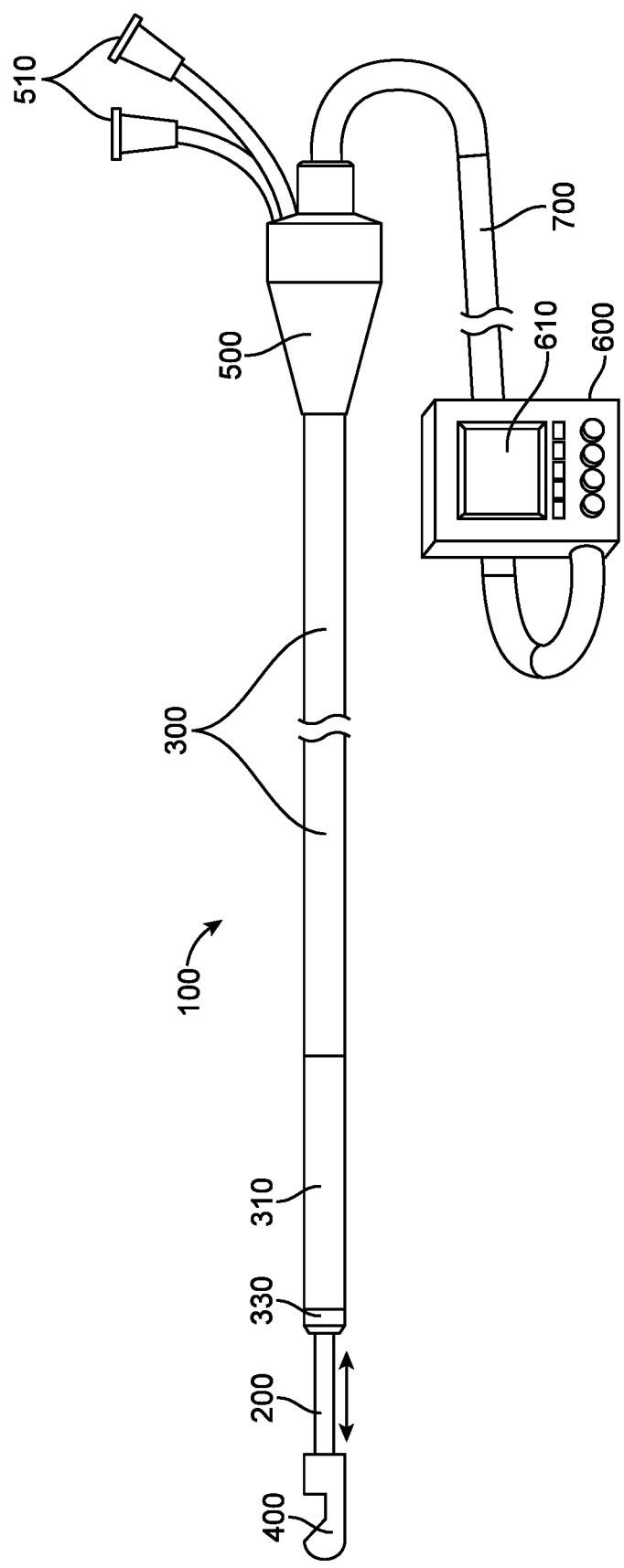
Figure 1C:
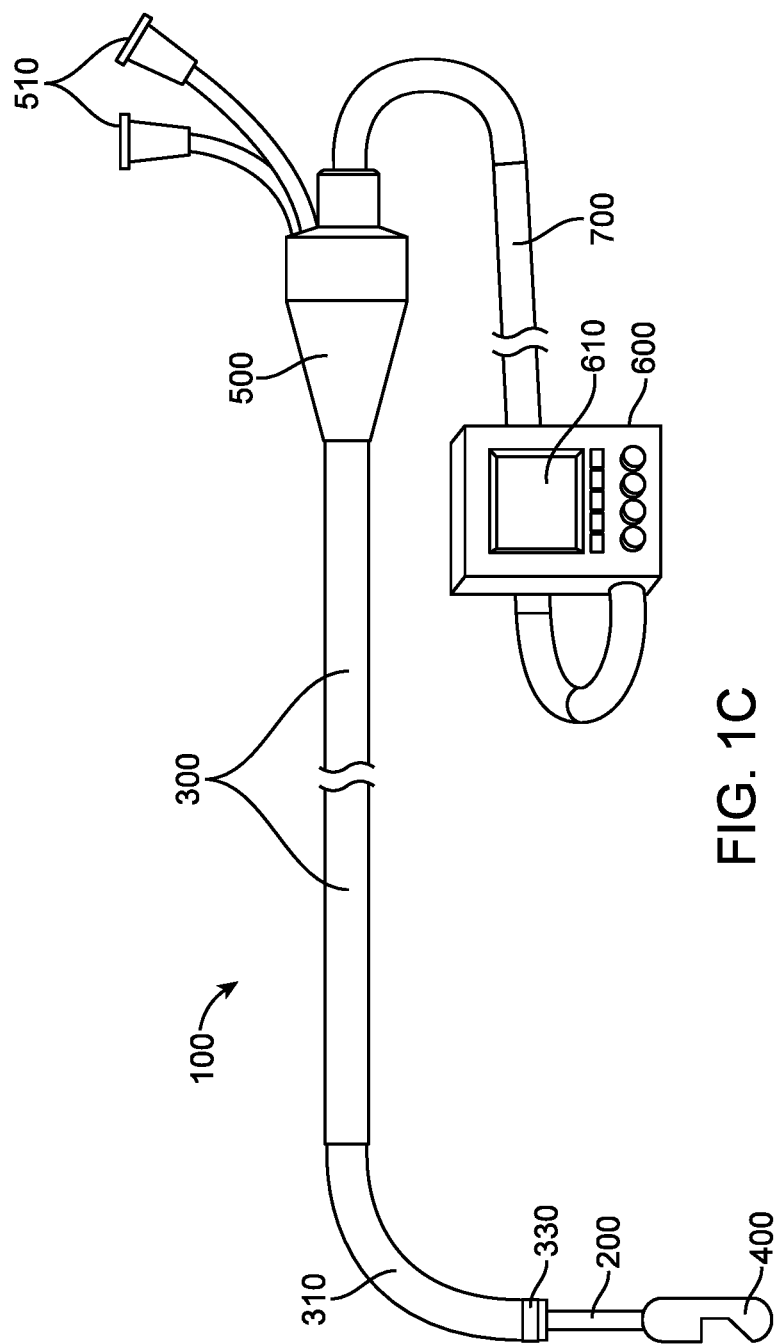

The outer shaft 300 of the catheter 100 can include a deflectable region 310 as shown in FIG. 1C. The outer shaft 300 may be constructed of varying stiffness of materials to provide a relatively stiffer proximal section and more flexibility in the deflectable region 310, for example a high durometer polymer in the proximal region and a lower durometer polymer in the distal region. Multiple polymers and/or material thicknesses and properties may be used to accomplish varying stiffness. Additionally, continuously varying stiffness may be used. A very soft distal tip may also be comprised by varying stiffness and/or thickness in materials. Materials may also be layered over each other to accomplish the desired properties. Materials comprising the components used in the construction of the outer shaft 300 and/or elongated member 200 may be made from materials that are radiopaque under fluoroscopy and/or visualized by various imaging modalities (e.g. metals, polymers with radiopaque fillers, etc). The outer shaft 300 may include an additional structural element 340 or elements to provide the desired torque and flexibility properties including braided and coiled materials (e.g. metal, fiber, etc). Structural elements may be or similar or dissimilar materials and constructions, e.g. a braid in the proximal region and a coil in the distal region of the outer shaft 300.

Figure 1D:
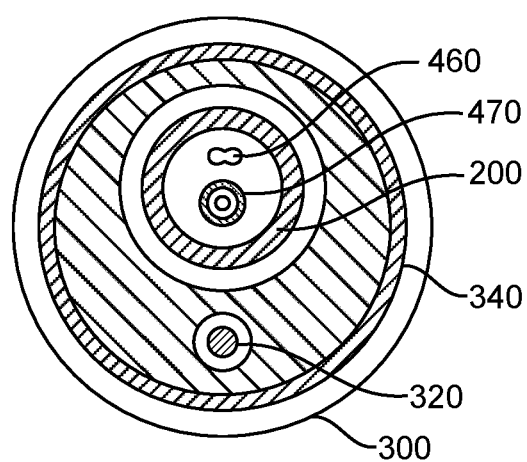
FIG. 1D shows a cross-section of the catheter of FIG. 1A-C taken at line segment A-A from FIG. 1A.

The outer shaft 300 and/or handle 500 can include a bending mechanism or mechanisms for bending the deflectable region 310 of the outer shaft 300 which may include a deflection element 320. The bending mechanism may include but is not limited to lengths of wires, ribbons, cables, lines, fibers, filament, combinations thereof, or any other actuating or force transmitting member. In one implementation the bending mechanism includes one deflection element 320 comprised of two materials, for example, a distal Nitinol region and a proximal Kevlar filament region. A variety of attachment elements and positions for connecting the bending mechanism and the elongate member are envisioned. FIG. 1D is a representative cross-section taken along the line A-A in FIG. 1A, of the outer shaft 300 showing the elongate member 200, a deflection element 320 (e.g. pull wire), and a structural element 340. The deflectable region may bend in one or multiple planes and be comprised of one or more deflectable segments giving the option of multiple degrees of freedom. The elongated member 200 may be constructed using similar methods and materials as described for the outer shaft 300 and may also be deflectable. To enhance the torque transmission of the elongate member 200 and/or outer shaft 300 may be constructed with counter wound coils made for example of flat, round, box section materials such as stainless steel. Radiopaque bands and or visual markers may be placed along the outer shaft 300 and/or elongate member 200). For example, a radiopaque band near the proximal end of the deflectable region 310 and one or more visual markers on the outside of the outer shaft 300 at specific distances from the end or an element of the catheter to aid in positioning of the catheter 100.

The deflection element 320 may be connected m the distal portion of the deflectable region 310 to a radial band 330 to serve as an anchor. The radial band 330 may be radiopaque to provide visualization under fluoroscopy. Similarly, attachment of the deflection element 320 may include but is not limited to using: adhesive, welding, pins, and/or screws or the like. Proximally, the deflection element 320 may be terminated in the region of the handle and be actuated by one or more ways of moving the detection element 320, for example screw(s), slider(s), gear(s), pulley(s), motor(s), electrical coil(s), and the like or combinations thereof. Position of the deflection element 320 or a portion of the catheter 100 may be desired. The use of a sensor or sensors may be used to accomplish this. Examples of sensors include but are not limited to optical, electrical, mechanical, magnetic, hydraulic, wireless, etc Information from the sensors may be used to inform and/or modify system parameters and/or control features (e.g. intensity, speed, position, pull wire position or tension, motor position, etc).

The elongate member 200 and outer shaft 300 may rotate and/or translate with respect to each other. FIG. 1A shows the distal assembly 400, attached to the elongate member 200 in a somewhat retracted position with respect to the outer shaft 300. It is within the scope of the invention that the distal assembly may retract within the outer shaft 300 and that distal assembly 400 and elongated member 200 may be fully retractable or removable from the outer shaft 300. FIG. 1B shows the elongate member 200 and distal assembly 400 extended from the outer shaft 300 relative to the position shown in FIG. 1A. Movement of the elongate member 200 with respect to the outer shaft 300 may be actuated and/or controlled and/or monitored in the handle 500 and/or controller 600. Rotational and/or translational movement may be accomplished by moving the elongated member 200 and/or outer shaft using, for example screw(s), slider(s), gear(s), pulley(s), motor(s), electrical coil(s), and the like or combinations thereof. Rotation and/or translation of elements of the catheter 100 (e.g. distal assembly 400) may be desired to form tissue necrosis in various shapes, including but not limited to individual or combinations of continuous and/or intermittent lines (e.g. open, closed, crossing, etc), shapes, spots, patterns (e.g. spiral, helix, dashed lines, etc) as will be described in more detail in FIGS. 7A-D. Position of the either of both of these elements may be desired. The use of a sensor or sensors may be used to accomplish this. Examples of sensors include but are not limited to optical, electrical, mechanical, magnetic, hydraulic, wireless, etc. Information from the sensors may be used to inform and/or modify system parameters and/or control features (e.g. intensity, speed, position, pull wire position or tension, motor position, etc).

Control of the movement of any component of the catheter 100 may be accomplished by physical inputs and/or by use of a controller 600. These movements may be for example: pre-programmed, auto or semi-automated, input manually, or a combination thereof. Control of the energy delivery may also be in part controlled by the controller 600. The controller 600 may incorporate an integral or separate display 610 which may have touch screen inputs and/or soft keys. The controller 600 and/or display 610 may have various inputs and/or outputs, for example: power in, alarms, visual display(s) (e.g. display 610), energy control, position of catheter 100 element or elements (e.g. distal assembly 400—longitudinal and/or rotational), sensor input/output, power out, control of actuating elements, tissue necrosis shape or pattern, energy delivery ON/OFF, time of use, energy setting, energy delivered, tissue structure depth (s), nerve(s) location, calcified tissue, progression of lesion formation, indicator of lesion completion, external and/or additional equipment control (e.g. pumps), safety stops and limits, etc.

The ability to regulate the use of the system and/or catheter 100 may be accomplished in, for example, the controller 600 or handle 100 where software and/or hardware monitors the use of the catheter 100 and only allows it to be functional for a determined amount of time and/or uses and/or energy delivery and the like. For example, once the catheter 100 delivers energy for the first time, there is a 4-hour clock which is started which after that has expired, the catheter 100 is no longer recognized by the controller 600 as being usable.

Information from an element or elements of the system (e.g. energy delivery apparatus 410) may be used for imaging and/or analysis of tissue (further referred to as "imaging") in or by the controller 600 and/or a separate component or instrument (not shown). This element or elements may be the same or different from the element or elements used to deliver energy to create necrotic tissue. Information from the element or elements may be used to determine distance from the element to a structure, to gather information about the structure or structures (e.g. thickness, morphology, physiology, multiple structures, structure recognition, tissue type, etc.), and other uses. Further this element or elements may be used to monitor the progression of a lesion while the lesion is created to titrate the energy delivered and/or stop energy delivery when the targeted lesion dimensions are achieved. In addition, the information gathered may be used to affect the energy delivered, including but not limited to intensity, duration, power, frequency, speed, etc, as well position of energy delivery. Examples include measuring wall thickness to determine energy dose parameters and identifying structures (e.g. nerve tissue) to determine energy delivery position. Imaging may be used to identify received echoes that are indicative of calcified regions where reflections are stronger than non-calcified tissue. Therapy power and intensity levels may be increased in these regions to insure effective therapy. Additional manual or automated guidance from the controller 600 and display 610 may direct the therapy to regions without substantial calcification as to insure effective therapy.

Imaging may be accomplished independently or interleaved with the delivery of therapeutic energy. It is intended that the imaging energy level or time of energy delivery is such that an insufficient amount of energy is deposited in the tissue to damage the tissue (e.g. create thermal damage and/or tissue necrosis) from the imaging. With respect to wall thickness, an ultrasound wave may be delivered to the tissue by an energy deliver element 410, in this case an ultrasound transducer or transducers. The varying tissues and tissue interfaces reflect back energy, which is then received by the ultrasound transducer(s) or other transducers, and the delay time is used to calculate the relative tissue positions (e.g. blood vessel inner and outer wall). From this, the wall thickness can be calculated and the energy delivery parameters can be adjusted, for example by the controller 600 and/or by the operator or a combination thereof, to ensure the appropriate depth of tissue necrosis is created from both an efficacy and a safety perspective. The energy delivery parameters can be adjusted prior to therapeutic energy delivery and/or during therapeutic energy, while the energy delivery apparatus is held in a specific position or is being moved with respect to the tissue (e.g. creating a line of tissue necrosis).

Imaging can be used to determine the properties of tissues. As tissue necrosis is being created, the acoustic properties of the tissue changes. This can be evaluated to determine among other things, for example if the tissue is healthy, necrotic, the depth of necrotic tissue, and the like. As different structures have different acoustic properties such as nerve tissue compared to the blood vessel wall, these structures can be differentiated using similar imaging techniques. In this manner for example, nerve tissue can be identified and specifically targeted with therapeutic energy. It is envisioned that combinations of energy delivery and imaging can be combined to produce the desired results.

The imaging and/or therapeutic information may be wholly or partly used in an image (e.g. 2 dimensional, 3 dimensional, layered, integrated) that may be static, dynamic, interactive, etc and shown on the display 610.

The imaging may further incorporate coded excitation and reception for improving the signal-to-noise (SNR) ratio and/or improve the spatial resolution.

In another aspect of the present invention, the catheter and/or system may be constructed as to be visualized and/or recognized by and/or interface and/or integrated with additional equipment, including but not limited to fluoroscopy, pumps (e.g. fluid), computed tomography, magnetic resonance imaging, anatomical mapping, electrocardiogram, respiration, pumps, imaging, etc. Control of a pump(s) may be used to deliver fluids (e.g. cooling, drugs, etc) along or through elements of the catheter 100, for example: cooling fluid through the elongate member 200, saline through the outer shaft 300, etc. A pump or pumps may be integrated with the controller.

The outer shaft 300 may be free to be moved at least in part rotationally and/or translationally with respect to the elongate member 200 by the proximal end of the outer shaft 300) terminating distal to the proximal end of the elongate member 200. Fixing the position between the two elements may be accomplished by using a seal, valve, locking mechanism, friction device or component or fit, etc and the like on one or more components.

Various details, features and uses of this embodiment include those as described herein regarding other embodiments.

Figure 1E:
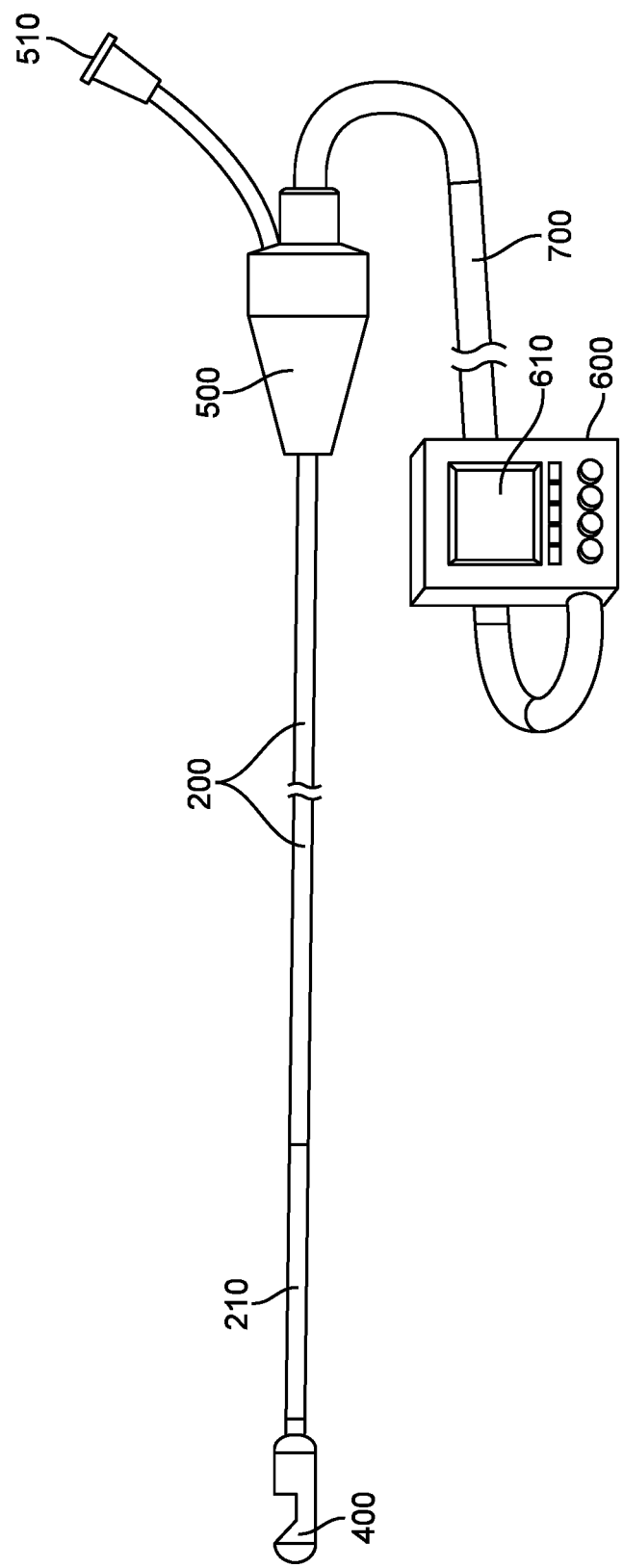
FIG. 1E shows a side view an additional version of a catheter in one embodiment of the invention.

FIG. 1E shows an alternate embodiment of the invention wherein the catheter 100 does not have an outer shaft 300. The elongate member 200 may include an elongate member deflectable region 210. The catheter 100 may be sized to pass through and/or use a sheath and/or guiding catheter for placement in the desired treatment region, or it may be used as a stand-alone device. The elongated member 200 may be constructed using similar methods and materials as described for the outer shaft 300. Various details, features, and uses of this embodiment include those as described herein regarding other embodiments.

Figure 1F:
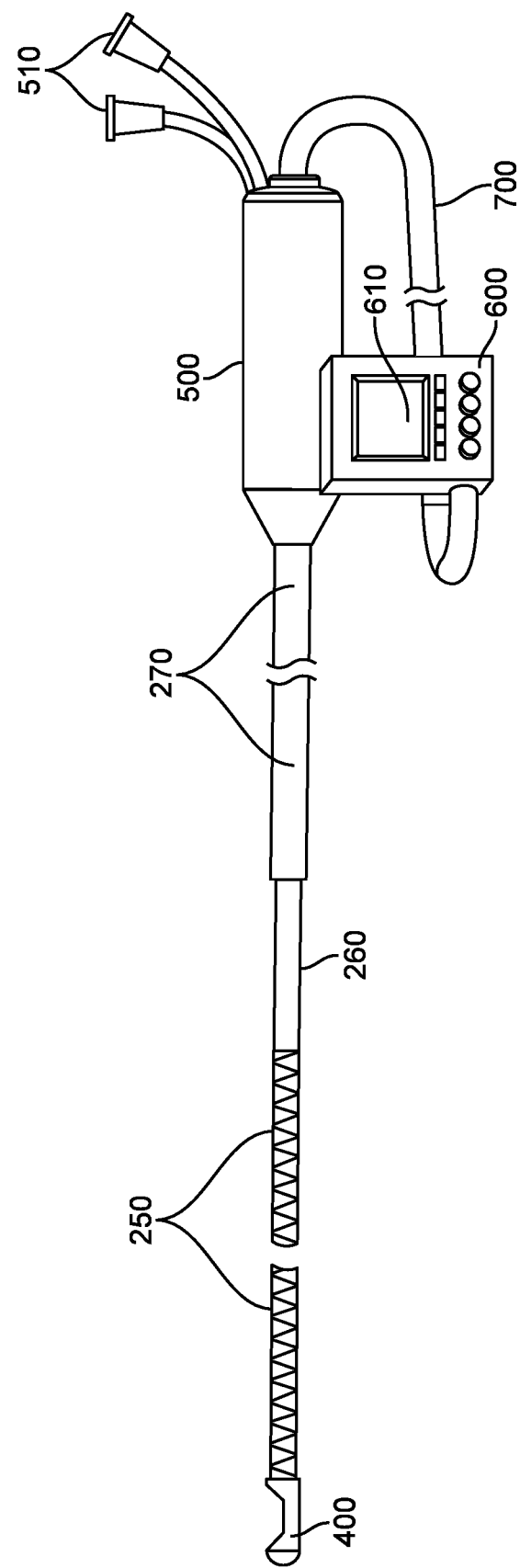
FIG. 1F shows as side view of an additional embodiment having an inner shaft constructed of one or more elements to accommodate varying stiffness, torqueability, and dimensions.

FIG. 1F shows another embodiment of the invention wherein the catheter 100 has a partial outer shaft with the catheter 100 sized to pass through and/or use a sheath and/or guiding catheter for placement in the desired treatment region, or it may be used as a stand-alone device. One example of the catheter shaft is constructed with an outer shaft 270 which may comprise one of more elements, and extend distally from the handle 500. The inner shaft may be constructed of one or more elements to accommodate varying stiffnesses, torqueability, dimensions, etc. As shown, the inner shaft comprises two elements, a proximal inner shaft 260 which is relatively stiffer, and a distal inner shaft 250 which is comparatively more flexible. Such elements may comprise coils, springs, support members, or sections of varying materials and geometries aimed towards altering local stiffness. The inner shaft may translate and/or rotate within the outer shaft 270. In this configuration, the catheter shaft may be inserted into a guiding catheter, a rotating hemostatic valve or Touhy-Borst adapter attached to the proximal end of the guiding catheter may be tightened down onto the outer shaft 270 to hold the catheter handle and outer shaft 270 in position with respect to the guiding catheter. This enables movement of the inner shaft with respect to the outer shaft 270 and guiding catheter. In this configuration, the guiding catheter may be placed within the desired treatment area (e.g. the ostium of a renal artery), the catheter 100 advanced through the guiding catheter until the distal assembly 400 is in position for imaging or therapy, the rotating hemostatic valve or Touhy-Borst adapter attached to the proximal end of the guiding catheter is tightened down onto the outer shaft 270, and then the movement of the inner shaft is controlled by the handle 500 and/or controller 600. Various details, features, and uses of this embodiment include those described herein regarding other embodiments.

FIGS. 2A-E show representative examples of various embodiments of the distal assembly 400 with a single element energy delivery apparatus 410. A single element energy delivery apparatus 410 is shown in these embodiments for tissue necrosis energy delivery and/or imaging, but more than one element, such as multiple ultrasound transducers, may comprise the energy delivery apparatus 410. For example, a single element energy delivery apparatus 410 may be used to create tissue necrosis while one or more (e.g. an array) of elements comprising the energy delivery apparatus 410 may be used for imaging.

Figure 2A:
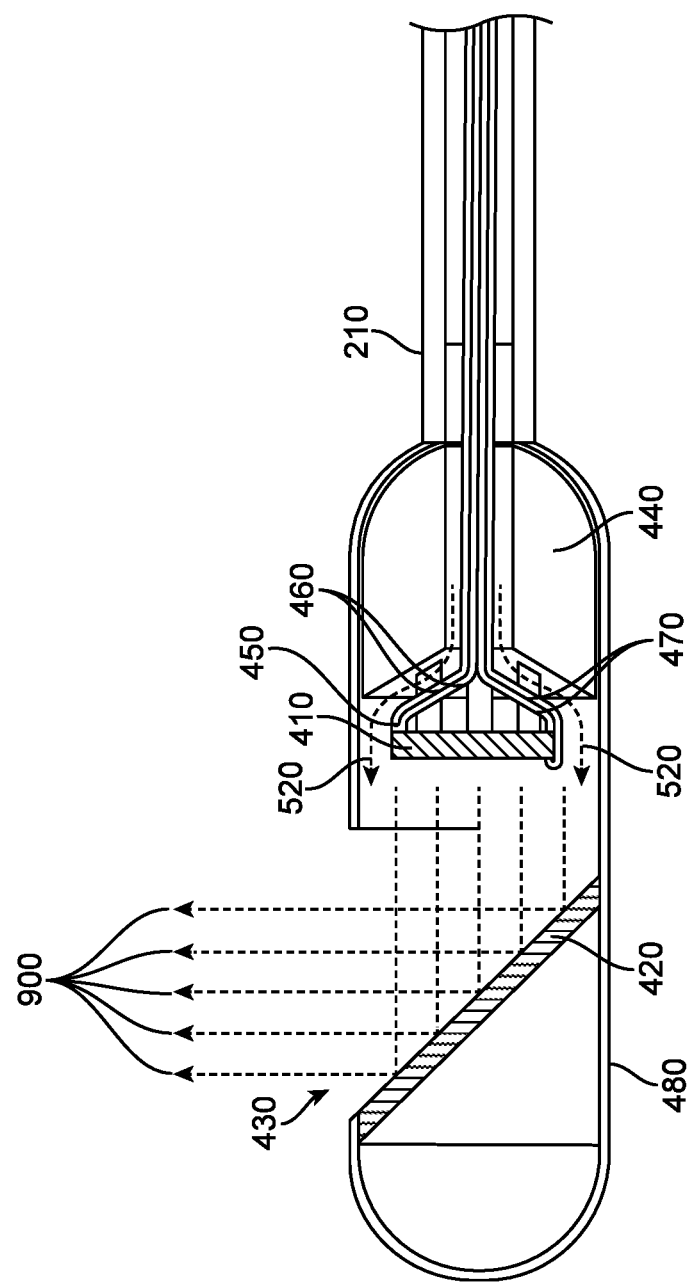
FIG. 2A shows a partial cross-section of a portion of the catheter encompassing the energy delivery apparatus in one embodiment of the invention.

FIG. 2A shows the distal assembly 400 with a single element energy delivery apparatus 410 in this embodiment being an ultrasound transducer. The ultrasound transducer can include energy delivery wires 470 or other means which carry the signal to the handle 500 and/or controller 600. As shown, the energy delivery wires 470 are a coaxial cable. The ultrasound transducer is set in the distal assembly 400 such that the ultrasound energy is directed towards a reflector 420. The distal assembly housing 480 can be made to be atraumatic in shape (e.g. rounded and/or smooth surfaces), and may include a recess portion or design feature(s) to prevent damage to the tissue when moving the distal assembly within the patient. The reflector 420 reflects ultrasound energy out of the distal assembly 400 through the aperture 430. One or more apertures may be used and any portion or all of the energy may be reflected. The ultrasound transducer is held in position by a support 440. The support 440 and/or energy delivery apparatus 410 may be moveable with respect to other parts of the catheter. e.g. the energy delivery apparatus 410 may be moveable with respect to the aperture 430. It is envisioned that the reflector 420 is planar, but can alternatively include a non-planar face, for example, a curved, convex, or concave surface. The angle of the reflector 420 can range below 180° In one implementation the angle is substantially 0-90°. In another implementation the angle is substantially 30-60°. In another implementation the angle is substantially 40-50° In a further embodiment the angle is substantially 45°.

During energy delivery, heat may be generated by the transducer. It is envisioned that the temperature can be controlled or affected by cooling the transducer. In one or more implementations cooling of the transducer can be accomplished by contacting the transducer subassembly with a fluid, for example, saline. In some implementations the transducer can be cooled using a fluid having a lower temperature relative to the temperature of the transducer. In one implementation a fluid for cooling the transducer is flushed past the transducer subassembly from a lumen in the catheter 100. Accordingly, as shown in FIGS. 1A-C, 1E, the proximal end of a lumen of the catheter 100 can be connected to a fluid port 510 or multiple fluid ports, for example, a luer fitting, in the region of the handle 500. For example, the fluid used for cooling the transducer can exit the distal assembly 400 through one or more openings and/or fluid can be passed through and/or around other components such as the outer shaft 300 and/or elongate member 200.

As shown in e.g. FIG. 2A, a temperature sensor 450 can be coupled with the energy delivery apparatus 410, for example, attached to the back side of the ultrasound transducer. The temperature sensor can be comprised of a thermocouple or a thermistor or any other suitable means. As shown in e.g. FIG. 2A, the temperature sensor 450 can include sensor wires 460 or other means which carry the signal to the handle 500 and/or controller 600.

As further shown in e g. FIG. 2A, the ultrasound transducer can be attached to the support 440 in such a manner as to create a void or pocket between the ultrasound transducer and the support 440. The void or pocket can include a material which efficiently reflects sound waves generated by the ultrasound transducer. The material of the void or pocket can be air or any other suitable material such as metal or plastic which reflects acoustic waves. Advantageously, the acoustic waves thus can be directed to exit from the front face of the transducer, resulting in a minimum amount of acoustic energy lost out through the transducer back side. Acoustic matching layers can be attached, through bonding, to the front surface of the transducer. The acoustic matching layers improve the efficiency of the transduction of electrical energy to acoustic energy, and vice-versa. This also reduces the heat produced by the subassembly.

Figure 2B:
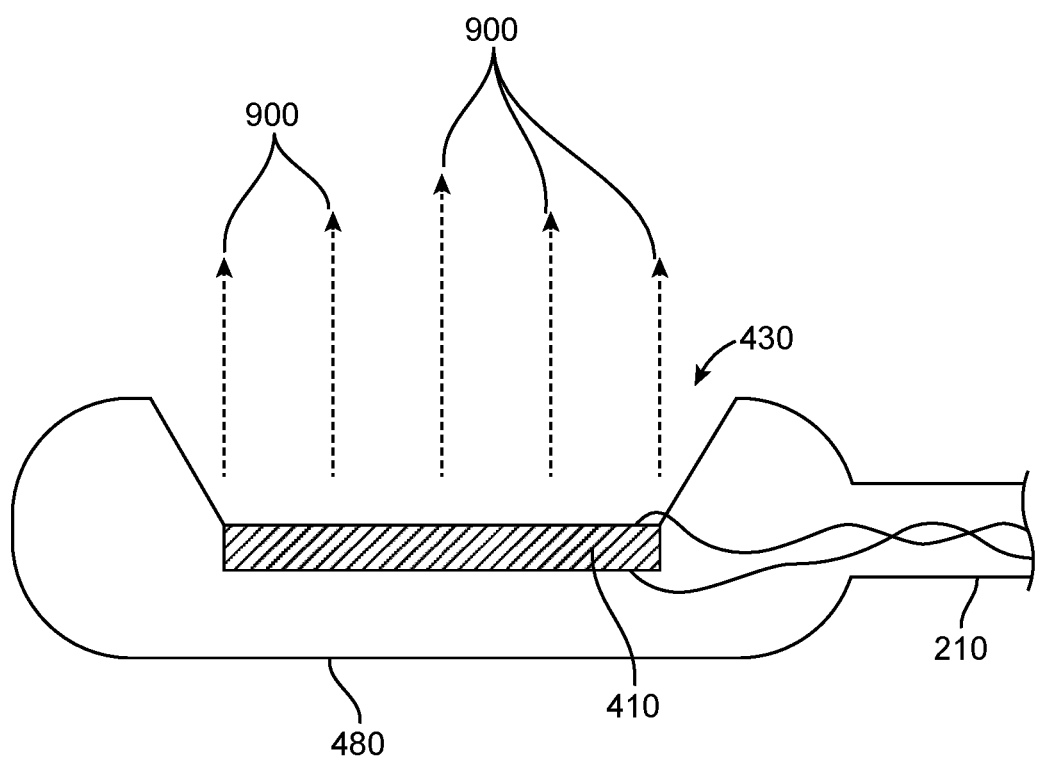
FIG. 2B shows a partial cross-section of an additional version of a portion of the catheter encompassing the energy delivery apparatus in one embodiment of the invention.

FIG. 2B shows a cross-section of an additional version of a portion of the catheter 100 encompassing the energy delivery apparatus 410. In this embodiment, the energy delivery apparatus 410 is positioned such that it is relatively aligned with the intended direction of energy delivery. In this configuration, the energy is delivered in a relatively radial direction, from less than 180 degrees to greater than 0 degrees, more preferably from 45 degrees to 135 degrees from the longitudinal axis. As shown the energy delivery apparatus is positioned within the housing 480 facing the aperture 430, however, it is envisioned that the energy delivery apparatus 410 can also be positioned at or on the surface of the housing. Various details, features, and uses of this embodiment include those as described herein regarding other embodiments.

Figure 2C:
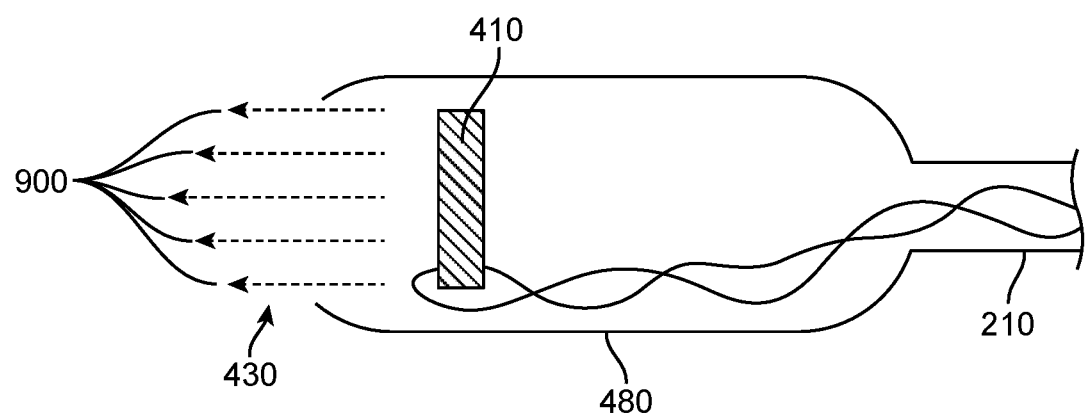
FIG. 2C shows a partial cross-section of an additional version of a portion of the catheter encompassing the energy delivery apparatus in one embodiment of the invention.

FIG. 2C shows a cross-section of an additional version of a portion of the catheter 100 encompassing the energy delivery apparatus 410. In this embodiment, the energy delivery apparatus 410 is positioned such that it is relatively aligned with the intended direction of energy delivery. In this configuration, the energy is delivered in a relatively longitudinal direction, from less than plus or minus 90 degrees from the longitudinal axis, more preferably from plus or minus 45 degrees. As shown the energy delivery apparatus is positioned within the housing 480 facing the aperture 430, however, it is envisioned that the energy delivery apparatus 410 can also be positioned at or on the surface of the housing. Various details, features, and uses of this embodiment include those as described herein regarding other embodiments.

Figure 2D:
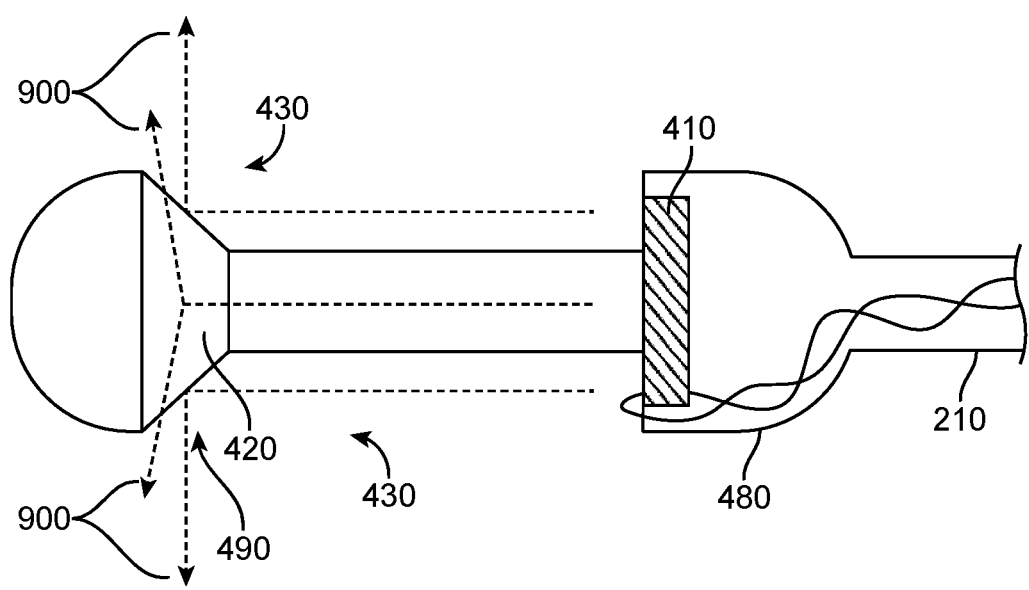
FIG. 2D shows a partial cross-section of an additional version of a portion of the catheter encompassing the energy delivery apparatus in one embodiment of the invention.

FIG. 2D shows a cross-section of an additional version of a portion of the catheter 100 encompassing the energy delivery apparatus 410. In this embodiment, the energy delivery apparatus 410 is positioned such that it is relatively aligned with a reflector 420 that directs the energy in a radial manner, creating an arc of energy delivery. In this configuration, the energy is delivered in a 360 degree arc, though it is envisioned that the arc can be more or less than 360 degrees as well as configured such that the arc is not all in a single plane, e.g. a spiral arc of energy. As shown, the arc of energy is in a relatively radial direction, from less than 180 degrees to greater than 0 degrees, more preferably from 45 degrees to 135 degrees. As shown the energy delivery apparatus is positioned within the housing 480 facing the reflector 420 which is held by the reflector housing 490. The reflector housing 490 may be attached to the housing 480 or other components of the catheter 100. Various details, features, and uses of this embodiment include those as described herein regarding other embodiments.

Figure 2E:
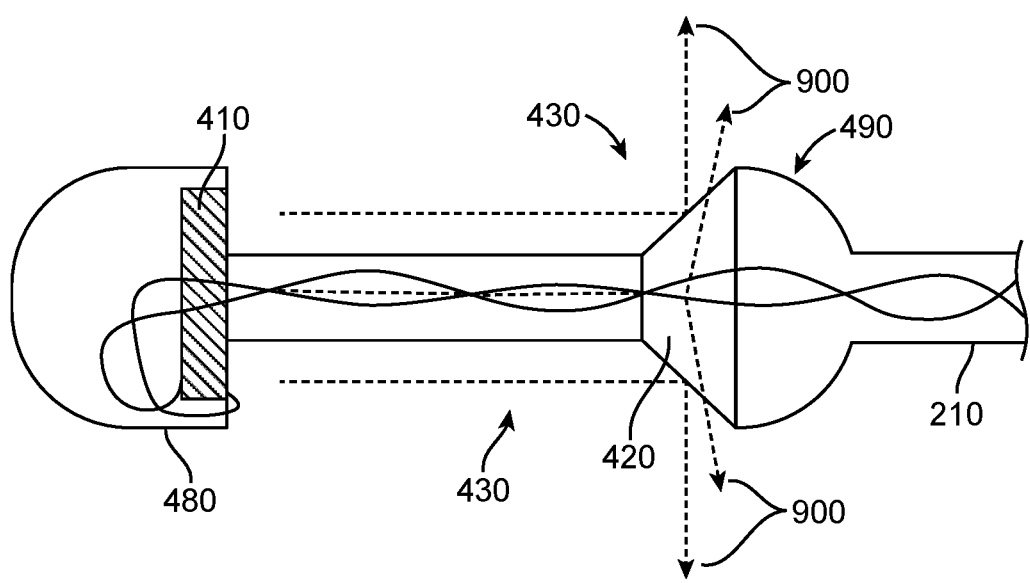
FIG. 2E shows a partial cross-section of an additional version of a portion of the catheter encompassing the energy delivery apparatus in another embodiment.

FIG. 2E shows a cross-section of an additional version of a portion of the catheter 100 encompassing the energy delivery apparatus. This embodiment is similar to that shown in FIG. 2D with the positions of the energy delivery apparatus 410 and the reflector 420 changed, in this case the energy delivery apparatus 410 is more proximal than the reflector 420. Various details, features, and uses of this embodiment include those as described herein regarding other embodiments.

Figure 2F:
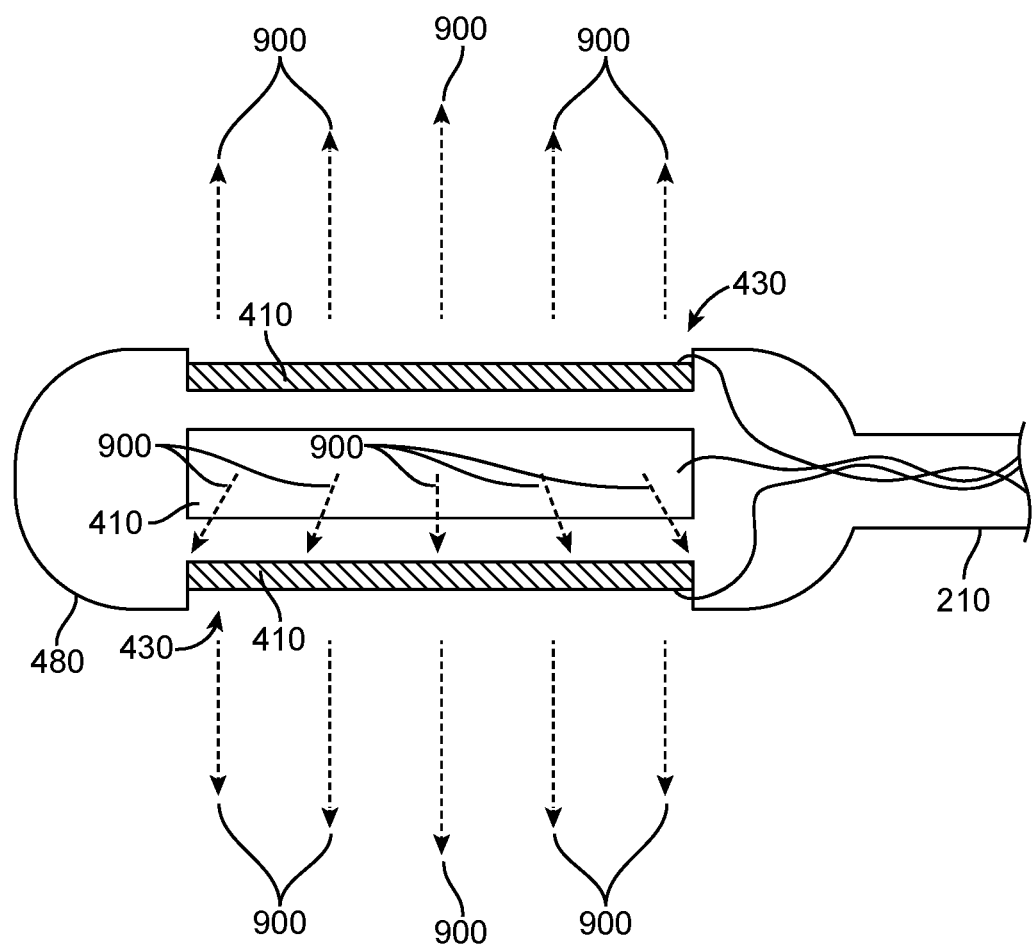
FIG. 2F shows a partial cross-section of an additional version of a portion of the catheter encompassing multiple energy delivery apparatus in another embodiment.

FIG. 2F shows a cross-section of an additional version of a portion of the catheter 100 encompassing multiple energy delivery apparatus 410. In this embodiment, a multiple element energy delivery apparatus 410 is positioned such that the elements are relatively aligned with the intended direction of energy delivery. As shown, the energy is delivered in a relatively radial direction, from less than 180 degrees to greater than 0 degrees, more preferably from 45 degrees to 135 degrees from the longitudinal axis, with the energy delivery apparatus 410 positioned within the housing 480 facing the aperture 430, however, it is envisioned that the energy delivery apparatus 410 can also be positioned at or on the surface of the housing. In addition, the energy delivery apparatus 410 may be positioned to create various patterns of energy for creating tissue necrosis and/or imaging as will be described in more detail elsewhere. Various details, features, and uses of this embodiment include those as described herein regarding other embodiments.

Figure 2G:
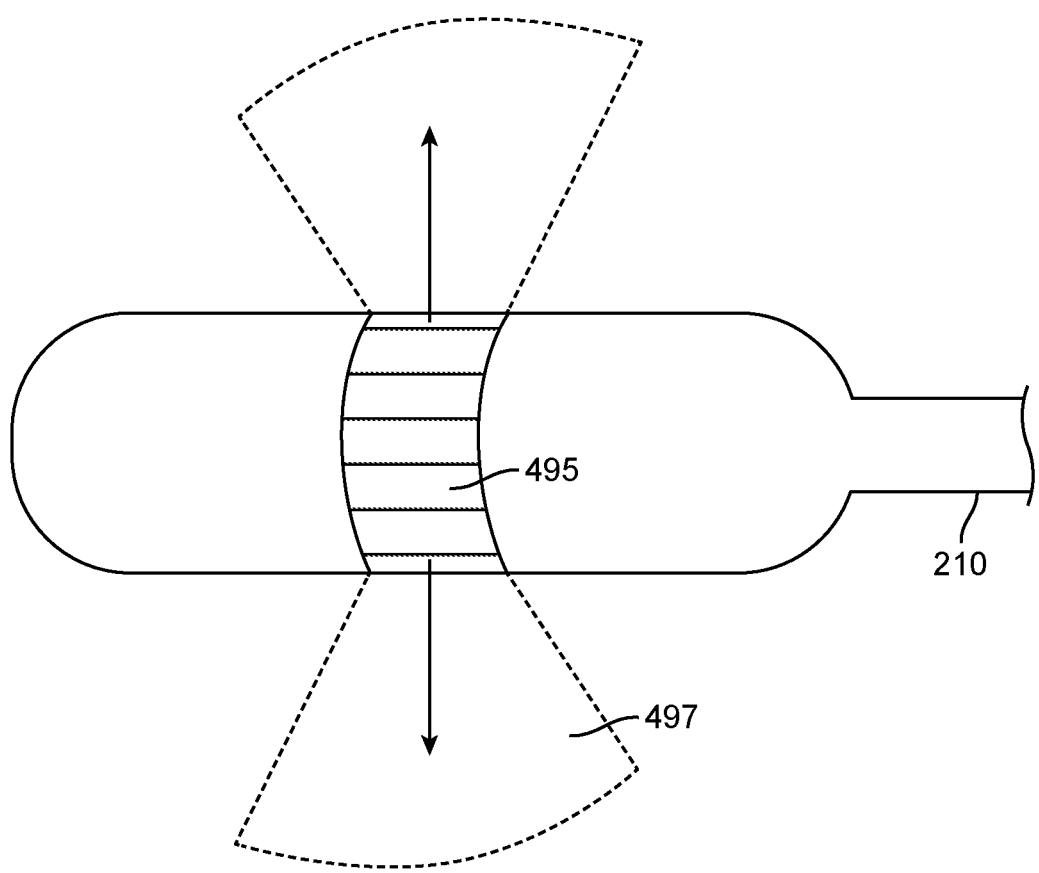
FIG. 2G shows a partial circumferential surface view of an additional version of a portion of the catheter encompassing further energy delivery apparatus in another embodiment.
Figure 2H:
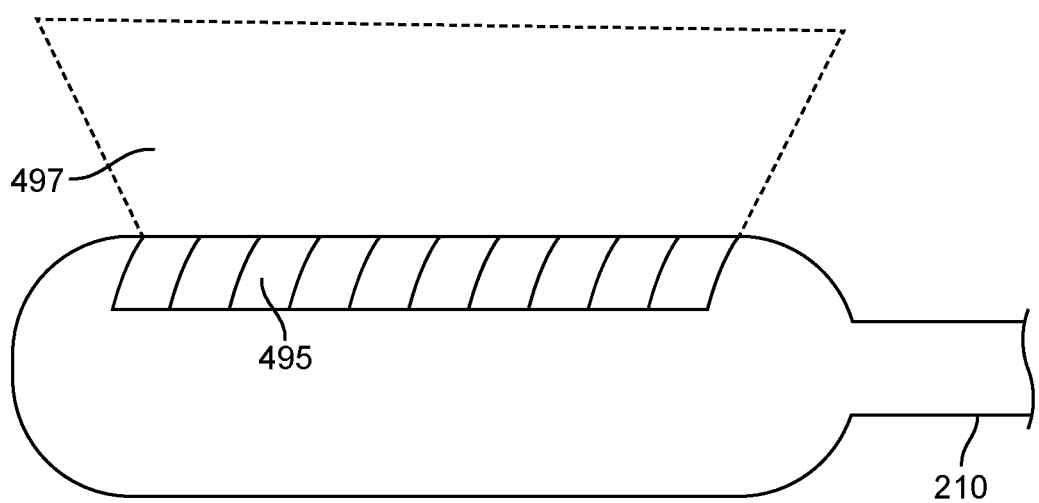
FIG. 2H shows a partial circumferential surface view of an additional version of a portion of the catheter encompassing further energy delivery apparatus in another embodiment.

FIGS. 2G and 2H each show a partial circumferential surface view of an additional version of a portion of the catheter encompassing furthering of the energy delivery apparatus in one embodiment of the invention. In addition to the energy delivery apparatus shown in FIGS. 2A-2F a one-dimensional, or two-dimensional, array of transducer elements may be used to image the tissue before therapy delivery and/or during therapy delivery as described within the context of "imaging". When used to monitor lesion formation the imaging plane 497 or section of the imaging plane can be positioned within the beam 900 used for therapy where the latter therapy beam is distal to the imaging plane 497 per FIGS. 2A-2F. The width of the imaging plane 497 (from acoustic diffraction) can overlap the therapy beam 900 if placed in close juxtaposition as in FIG. 2G or the imaging plane 497 may be steered electronically to reach more distally as show in FIG. 2H. Example energy delivery apparatus configurations for one-dimensional and two-dimensional arrays are shown in FIGS. 9B and 9C. Two-dimensional arrays (FIG. 9C) can steer distally into the therapy beam 900 in either preferred orientations as shown in FIGS. 2G and 2H if the one dimensional array 495 (as represented in FIG. 9B) is replaced with a two dimensional array 495 (as represented in FIG. 9C).

Figure 3:
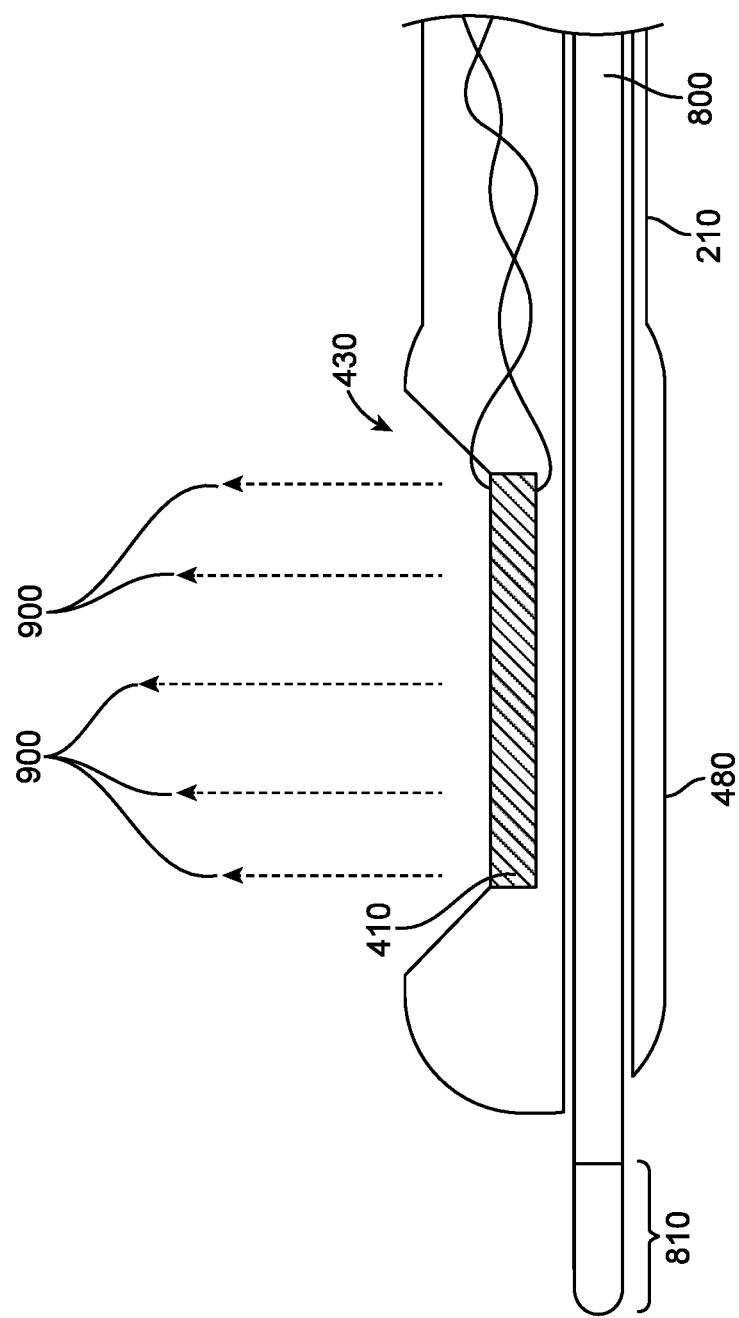
FIG. 3 shows a partial cross-section of a catheter distal section including a guide wire in another embodiment.

FIG. 3 shows an additional catheter 100 distal section in another embodiment. In this embodiment all or a portion of the catheter 100 is used with a guide element 800. The guide element 800 may be a guide wire. The guide element 800 may have a distally positioned guide element tip 810. The guide element tip 810 may be flexible, shapeable, atraumatic, and the like. As shown, the guide element 800 is passed through distal assembly 400 and the elongate member 200 for at least a portion of its length. The guide element 800 may be fixed in position, relatively fixed in position (e.g. movable within a limited range of motion in one or more directions), or free to move with respect to other components of the catheter, including being partially or completely removed from the catheter 100.

In various embodiments, recessing the energy delivery apparatus 410 may be advantageous to cooling the energy delivery apparatus 410, as well for providing a fluid and/or cooling fluid barrier between the energy delivery apparatus 410 and the blood. Features of the reflector 420 and/or the housing 480 and/or other additional elements may be used to create various patterns of energy as will be described in more detail elsewhere.

In various embodiments, the aperture 430 or apertures can be in part or completely covered and/or filled with an energy transparent and/or semi-transparent material. Additionally, components of the catheter 100 may be in part or entirely coated. The coating may be for example but not limited to: lubricious, anti-thrombogenic, biocompatible, and the like.

Figure 4A:
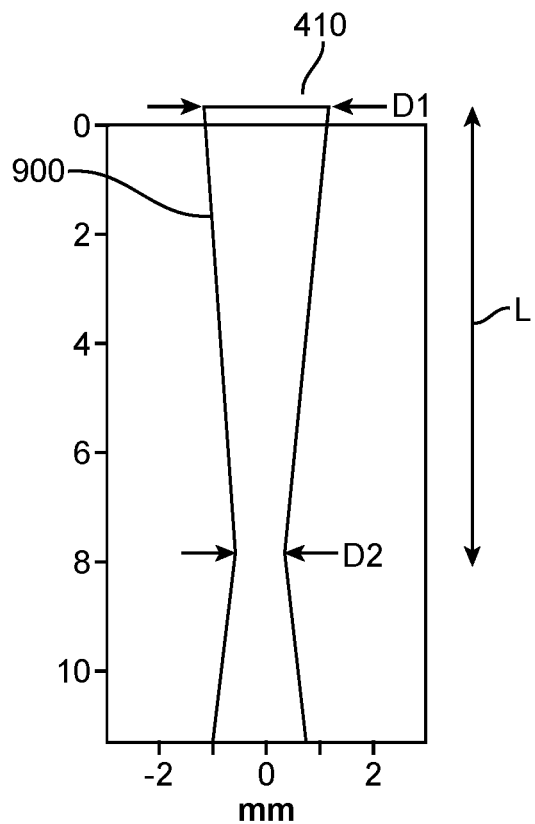
FIG. 4A shows a representative energy beam profile in embodiments of the invention.

FIG. 4 shows a cross-section of a representative energy beam profile in one of more embodiments. In this embodiment the energy is ultrasound. As shown, the diameter of the ultrasound beam at the ultrasound transducer face is equal to, or less than, the diameter D1 of the ultrasound transducer. For a flat disc transducer, the ultrasound beam 900 converges slightly from the ultrasound transducer face out to a distance of L, beyond which the beam diverges with the minimum beam width D2 occurring at distance L. For example, in the renal arteries where the ultrasound transducer face may be less than 5 mm from the vessel wall, with an arterial wall thickness of 0.4 mm, the above beam of similar diameters D1 and D2 may be collimated as to avoid a tight focus of increased intensity. A collimated beam delivers a substantially similar level of intensity over a distance that includes the vessel lumen and the tissue beyond the intimal lining that is targeted for treatment. An example ultrasound beam is one with a frequency of 11 MHz and a transducer diameter of 2.0 mm providing a minimum beam width D2 of 0.8 mm at a distance of 7 mm. Various ultrasound transducer widths, shapes, and frequencies can be used to create the desired beam profile. The transducer or transducers may further be recessed within the housing 480 to move the maximum distance of energy divergence to a distance that insures a collimated beam will target the tissues of interest and the maximum distance of sufficient energy density is not too deep into the tissue. In addition, the use of a lens or lenses as well as multiple transducers can be used to modify the beam profile as well, for example, to provide for a narrower or a wider region of tissue necrosis. The lens or lenses could be attached to the transducer or other component on the catheter 100 (e.g. the housing 480).

Figure 4B:
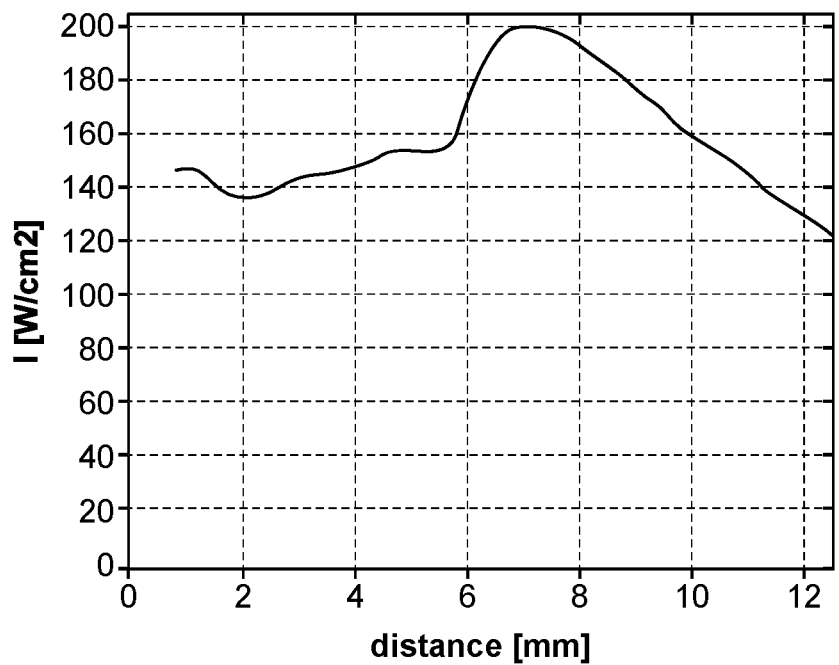
FIG. 4B shows an acoustic intensity profile as a function of distance from the energy delivery apparatus in various embodiments.
Figure 5:
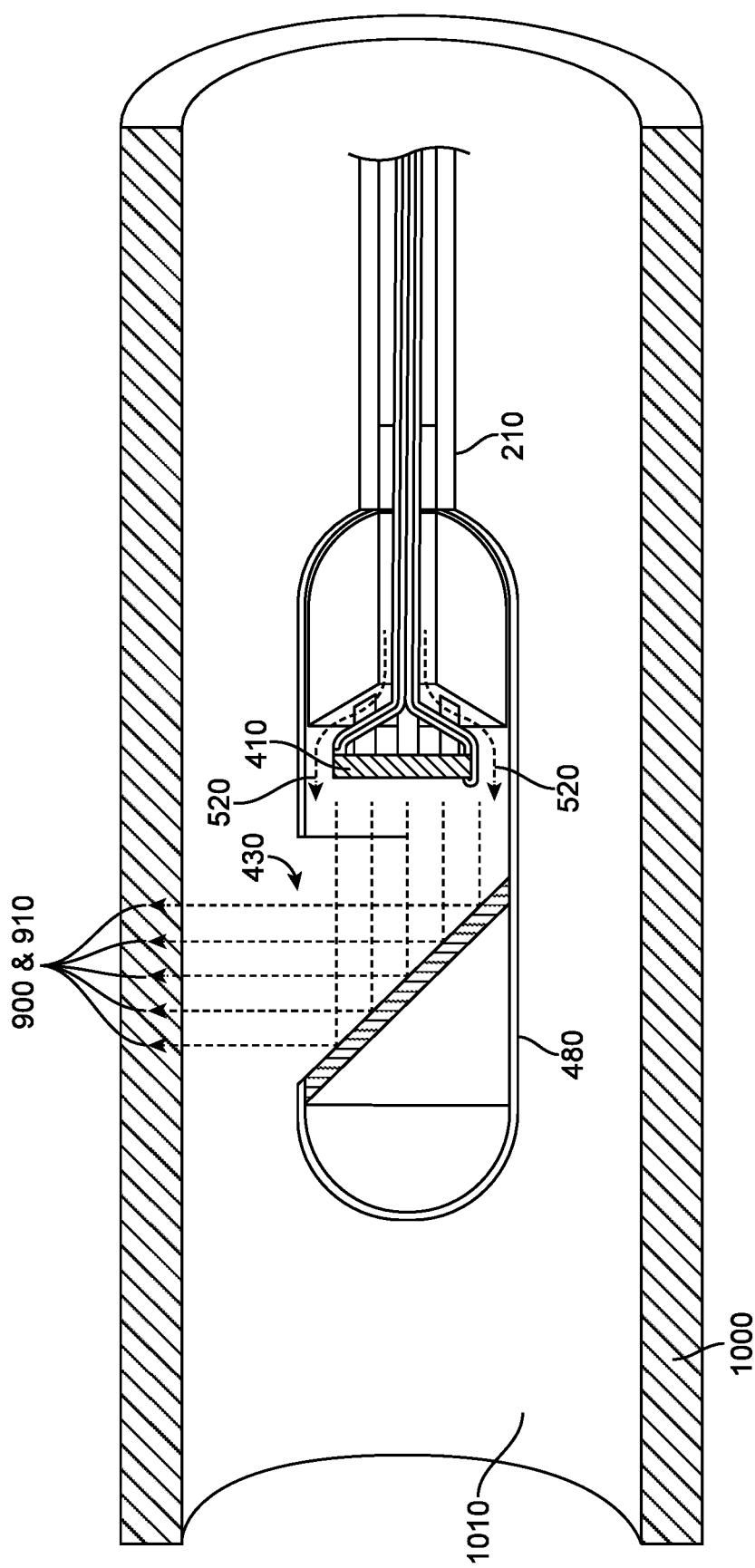
FIG. 5 shows a partial cross-section of a portion of the catheter encompassing the energy delivery apparatus in a vessel in another embodiment.

Intensity levels from the beam of FIG. 4 may be controlled by adjusting the time-varying voltages to the element 410. Higher intensity levels produce more heat in shorter time durations than lower intensities Intensities for the embodiments herein are preferred to be less than 1000 W/cm$^2$ as defined by the spatial peak temporal peak intensity measured in water. Intensities above 1000 W/cm are avoided to eliminate potential mechanical tissue damage caused by cavitation and preserve more precisely controlled therapy from targeted thermal damage. Avoiding intensities above 1000 W/cm$^2$ also minimizes the creation of microbubbles that may reflect ultrasound and hinder effective uniform therapy delivery. Preferred intensities in the blood are under 750 W/cm. FIG. 5 shows the spatial average temporal average acoustic intensity in blood for a representative acoustic beam as shown in FIG. 4. The spatial average is defined as the spatial average within the beam at each distance defined over the extent where the intensity is above the −6 decibel level relative to the spatial peak intensity over all distances which is set to the zero decibel level. For relatively collimated beams the maximum spatial average temporal average intensity does not exceed twice the minimum intensity. For the example in FIG. 4B the beam remains substantially collimated down to a distance of 14 mm. Relatively collimated beams are designed through the choice of the acoustic element type, the element(s) dimensions, the mechanical mounting conditions, and the acoustic frequencies of operation. Electronic defocusing with multiple elements can produce collimated beams Mechanical lens may also be used to generate collimated beams.

FIG. 5 shows a cross-section of a portion of the catheter encompassing the energy delivery apparatus 410 in a vessel 1000 (e.g. blood vessel) in one embodiment of the invention. When ultrasound energy is delivered by the energy delivery apparatus, the energy can be used to create a motive force emanating from the face of the transducer resulting in acoustic pressure induced flow 910. This acoustic streaming from acoustic pressure induced flow 910 can interact with the fluid 520 being passed through the catheter 100 and/or with the blood to remove or reduce the amount of heat being generated at and/or near the tissue or vessel surface 1010, allowing for decreased damage at the vessel surface 1010, preserving the endothelial layer and/or at least a portion of the intima, thus increasing safety by reducing or eliminating, for example: thrombus formation, charring, restenosis, etc. Fluid 520 below body temperature (e.g. room temperature or cooled) can be used to increase the effect of removing heat from the tissue surface. Varying the rate of fluid flow can also effect the heat removal and higher fluid flows will remove heat more quickly.

As shown, the energy delivery apparatus 410 is not in contact with the target tissue. By generating an ultrasound beam with a given length of usable energy (as shown in FIG. 4), the energy delivery apparatus can be distanced from the target tissue causing little or no damage to the target and surrounding tissues, both from a contact perspective (e.g. abrasion) and from the fact there is little or no thermal conductivity from the catheter 100 to the tissue. This is in dramatic contrast to typical RF ablation catheters used for creating lesions that must not only be in contact with the tissue, but the pressure with which they are positioned against the tissue affects the amount of tissue necrosis, not to mention the potential for thrombus formation and charring also known to negatively affect that energy delivery technology.

One or more elements of the catheter 100 (e.g. distal assembly 400, housing 480, aperture 430, reflector 420) maybe be constructed to affect acoustic pressure induced flow 910, such as focusing the acoustic pressure induced flow 910 into a more narrow region or diverging it to cover a greater area.

Various details, features and uses of this embodiment include those as described herein regarding other embodiments.

Figure 6:
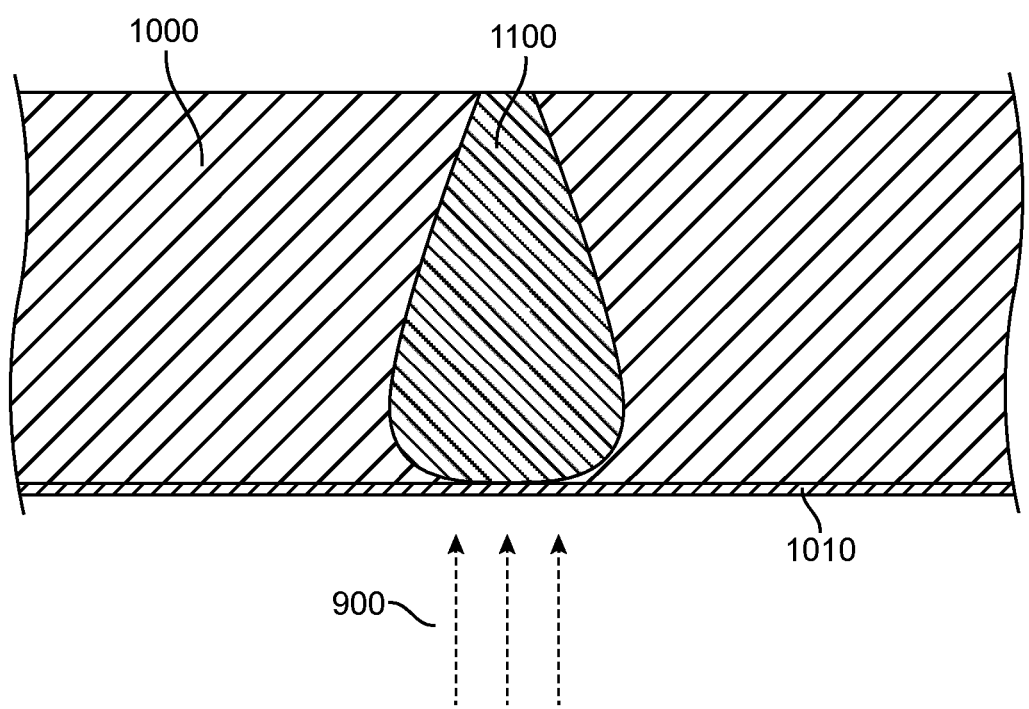
FIG. 6 shows a cross-section of a representative profile of necrotic tissue that may be created in various embodiments of the invention.

FIG. 6 shows the cross-section of a representative profile of a region of tissue necrosis 1100 that may be created with embodiments of this invention. As energy from an ultrasound beam 900 enters tissue, for example, a vessel 1000, the energy is absorbed and converted into heat. This causes the temperature of the tissue to rise, which is offset by the tissues ability to remove heat to due blood circulation, thermal dissipation, etc. As the energy travels deeper into the tissue, there is less energy available to be converted to heat as some of the energy has already been absorbed. As such, the width of a particular region of tissue necrosis 1100 will be wider near the entrance of the ultrasound beam 900 (e.g. the vessel surface 1010) and narrower farther away from it (e.g. deeper in the tissue 1000).

Blood flow within the vessel 1000 as well as acoustic pressure induced flow 910 increase the thermal transfer at the vessel surface 1010 from the vessel surface 1010 to the blood and/or fluid delivered by the catheter. This increased rate of heat removal reduces the thermal damage at the vessel surface 1010. This can be affected by, for example: the flow rate, velocity, and temperature of the fluid passed through the catheter 100 as well as the power, frequency, pulse rate, duration, etc of the energy delivered among other factors. If desired, these parameters can be tailored such that the endothelial layer of the vessel 1000 is not permanently damaged.

Tissue necrosis occurs when the tissue is heated above a temperature of 55 degrees Celsius. By adjusting the energy parameters the region of tissue necrosis 1100, particularly depth of the region, can be controlled. For specific applications, it may be desirable to cause necrosis through the entire tissue or wall of the vessel 1000, or only through a portion of the tissue. Accurate control of tissue necrosis and depth are particularly important when there is a tissue or structure on the far side of the target tissue that it is undesirable to cause damage to.

The ability to accurately control width and depth of the region of tissue necrosis 1100 provides for a safe and efficacious treatment. Being able to monitor changes within the tissue using imaging is an additional enhancement. Monitoring reflected amplitudes and the rate of change of these amplitudes can be used to monitor the progression of a thermal lesion. Changes in density and changes in the speed of sound can all be used to monitor treatment.

FIGS. 7A-D show cross-sections of vessels with representative shapes of necrotic tissue. These shapes serve only as examples of what can be created with embodiments of the invention. One such example of creating a region of tissue necrosis 1100 in a patient is as follows:

1. Inserting an introducer into a patient's femoral artery.
2. Inserting the catheter 100 through the introducer to the region of the patient's renal arteries.
3. Deflecting the deflectable region 310 of the outer shaft 300 to assist in selecting a renal artery.
4. Optionally, injecting a radiopaque dye through a lumen of the catheter 100, for example between the elongate member 200 and the outer shaft 300, sufficient to visualize the location of at least on renal artery.
5. Positioning the distal assembly 400 inside the renal artery and the distal end of the outer shaft 300 in the region of the ostium of the renal artery.
6. Optionally injecting a pain reduction medicament through a lumen of the catheter 100, for example between the elongate member 200 and the outer shaft 300, to decrease the pain associated with tissue necrosis. Optionally, the drug may be administered through the fluid path 520. Optionally, the drug may be further activated by delivering ultrasound to the tissue while the drug baths the intimal lining.
7. Advancing the distal assembly 400 a distance into the renal artery.
8. Selecting the shape of tissue necrosis desired on the controller.
9. Optionally selecting one or more energy delivery parameters and/or letting the controller determine one or more energy delivery parameters from stored data or real time imaging information.
10. Optionally using imaging to identify the renal nerves and selecting to deliver energy only to those positions along the vessel 1000.
11. Initiating tissue necrosis formation. Retracting and/or rotating the distal assembly while delivering energy and/or moving the catheter 100 into a position and then delivering energy, via operator input and/or semi-automatic control by the controller 600 and/or fully-automatic control to create the desired region of tissue necrosis 1100.
12. Optionally determining the extent of tissue necrosis while creating the region of tissue necrosis 1100.
13. Optionally displaying information on the display 610.
14. Optionally treating the other renal artery in a similar fashion.
15. Removing the catheter 100 from the patient.
16. Removing the introducer from the patient.

Figure 7A:
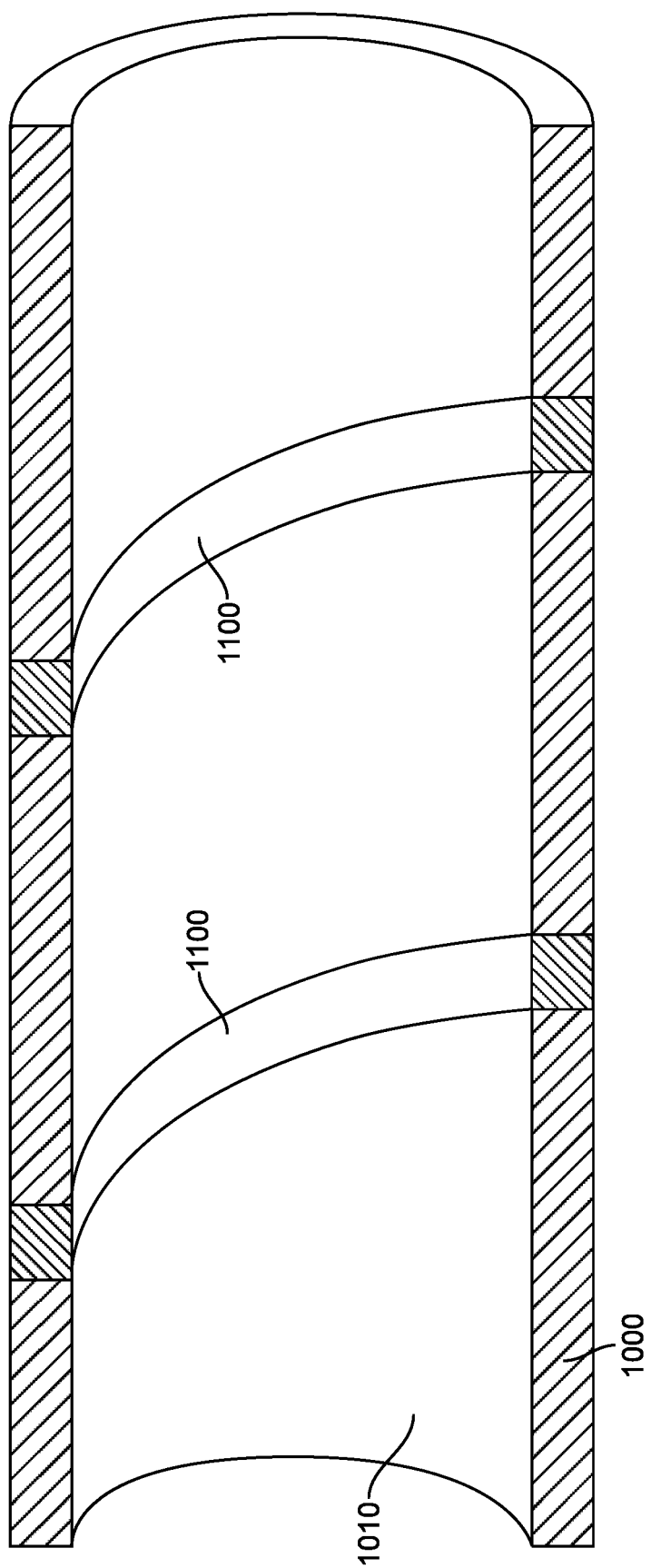
Figure 7C:
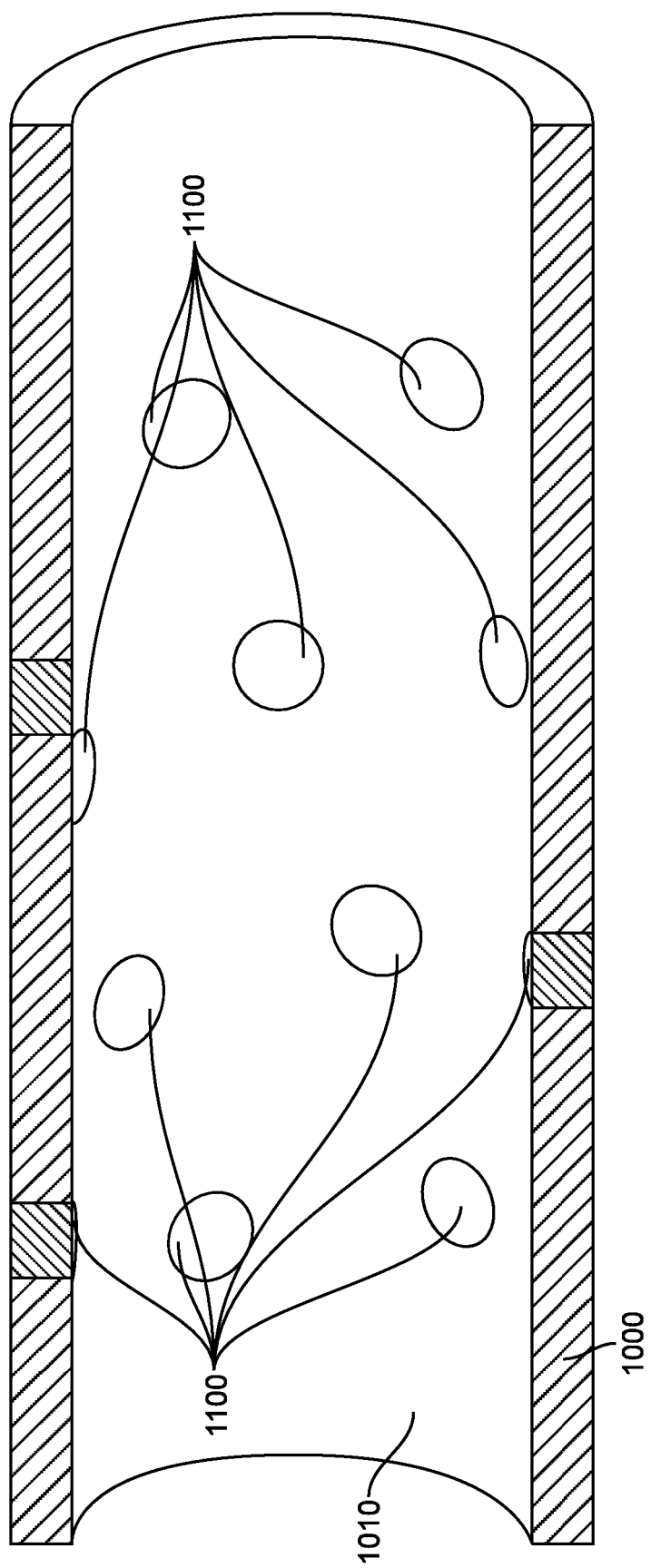

As described above, the distal assembly 400 is retracted, similarly it can be advanced or advanced and retracted and rotated if necessary to form the desired shape or shapes. The invention provides a system that is capable of creating regions of tissue necrosis 1100 that may be composed of one of more spots; lines of varying shapes, for example a spiral or helix; continuous or intermittent lines, circles, narrow or wide lines, and the like as well as combinations thereof. FIG. 7A shows a spiral region of tissue necrosis 1100. FIG. 7B shows multiple regions of tissue necrosis 1100 forming an intermittent spiral. FIG. 7C shows multiple regions of tissue necrosis 1100 forming a pattern of spots. FIG. 7D shows a circular region of tissue necrosis 1100.

The handle 500 and/or controller 600, for example, can be used to affect manual (e.g. operator input), semi-automatic, and/or fully-automatic control over various functions of the system, including but not limited to catheter 100 or catheter component movement, energy parameters, energy delivery, and imaging among others. Control in this manner allows for accurate placement and shape of the tissue necrosis pattern. By not having to manually reposition the energy delivery apparatus 410, the desired region(s) of tissue necrosis can be created in a more expeditious manner. Similarly, by having an energy beam the does not require tissue contact, the procedure can be conducted more quickly than if contact and/or a range of contact pressures is required.

Accurate tissue necrosis patterns with controlled width and depth, provides the operator with an easy-to-use system capable of quickly delivering an efficacious and safe therapy to the patient.

Figure 8:
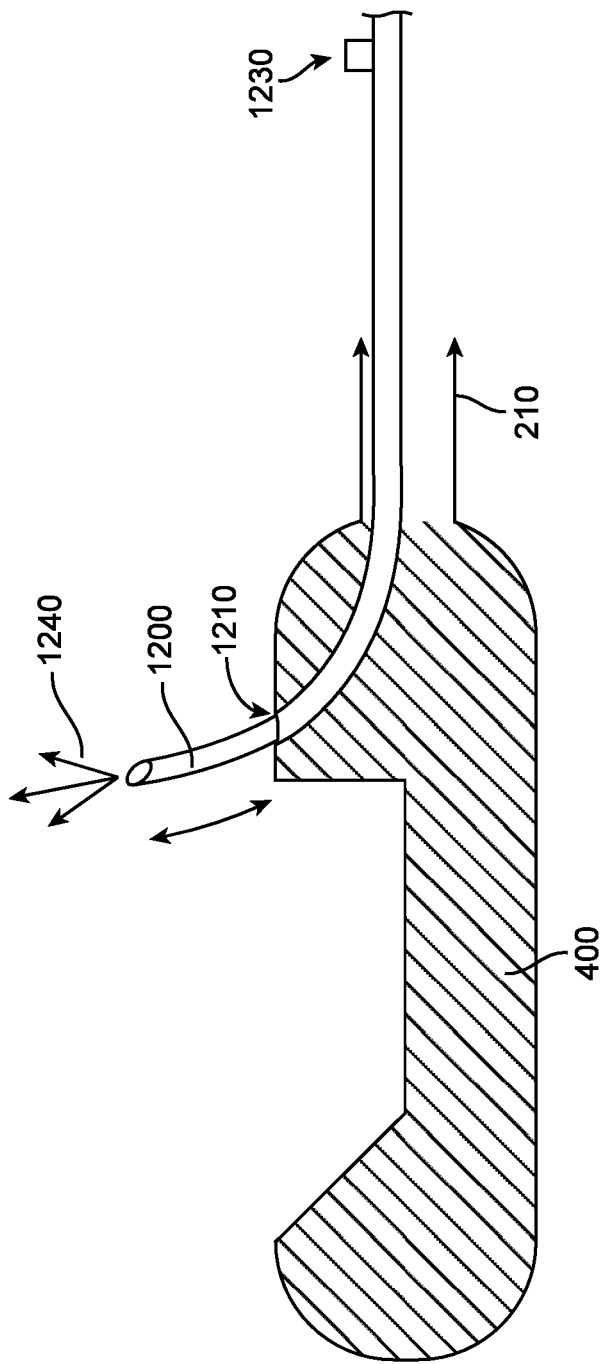
FIG. 8 shows a partial cross-section of a portion of the catheter encompassing the energy delivery apparatus and a component to enable pain reduction in an embodiment.

FIG. 8 shows a portion of the catheter encompassing the energy delivery apparatus and a component to aid in pain reduction in embodiments of the invention. During the creation of a region of tissue necrosis 1100, depending on the tissue, the patient may feel pain associated with the thermal rise of the tissue (e.g. nerve tissue). As such, it is desirable to affect a decrease in the pain associated with creating tissue necrosis.

A reduction in pain associated with creating tissue necrosis may be accomplished by delivering a pain reduction medicament or anesthetic or other fluid/gel/solid near the region of energy delivery or to a region that will affect the sensation of pain from the delivery of energy. The delivery of the pain reduction medicament or anesthetic or other fluid/gel/solid can take place prior to and/or during and/or after the delivery of energy. As seen in FIG. 8, a feature may be incorporated on the catheter 100 to aid in delivering a pain reduction medicament or other fluid to the site of energy delivery. In this example, a fluid delivery tube 1200 (e.g. a needle) is used to deliver a fluid (e.g. pain reduction medicament 1240) into the tissue near the region of energy delivery. The fluid delivery tube 1200, for example, can be retracted into the distal assembly 400 or component of the catheter 100 through the fluid delivery tube port 1210. In use, the fluid delivery tube 1200 can be retracted into the distal assembly 400 to enable atraumatic insertion and positioning at the intended site of energy delivery. Then fluid delivery tube 1200 can then be advanced out of the distal assembly 400 and positioned near or in the tissue either under manual control, such as by moving a fluid delivery tube actuator 1230 located more proximally on the catheter 100, or under some level of control by the controller 600 (e.g. semi-automatic, automatic). The fluid is then administered though the fluid delivery tube 1200 via a fluid delivery fitting 1220, such as a luer fitting and tube, located in a more proximal region of the catheter 100, for example on the handle 500.

Other features on the catheter 100 can be constructed for localized fluid/gel/solid delivery, for example, components of the catheter 100 such as the elongate member 200, outer shaft 300, and distal assembly 400 may have one or more openings or ports or features (e.g. barbs, sharp elements) to deliver the fluid/gel/solid at a point or points along the length of the catheter 100. As shown in FIGS. 1, 2, and 5, a fluid or gel can be passed through a lumen of the catheter 100, examples include: between the elongate member 200 and the outer shaft 300, through the elongate member 200 and out the distal assembly 400, etc. The fluid/gel can be mixed with the fluid used to remove heat from the energy delivery apparatus 410 and/or tissue as described previously. In certain cases, it may be desirable to inject other fluids/ materials into the tissue causing either damage or death to specific tissues. A fluid or component similar to the fluid delivery tube could be used to advance a solid out of the catheter through an opening or port. Various details, features and uses of these embodiments include those as described herein regarding other embodiments.

Further, the ultrasound from the energy delivery apparatus may also be used to stimulate the efficiency of the drug delivery through sonoporation, bursting or altering encapsulated drug delivery vehicles, and thermal stimulated drug delivery. Injecting the drug directly into the fluid path 520 can avoid a separate needle delivery vehicle and may be most efficiently directed to the intimal layer of interest.

Figure 9A:
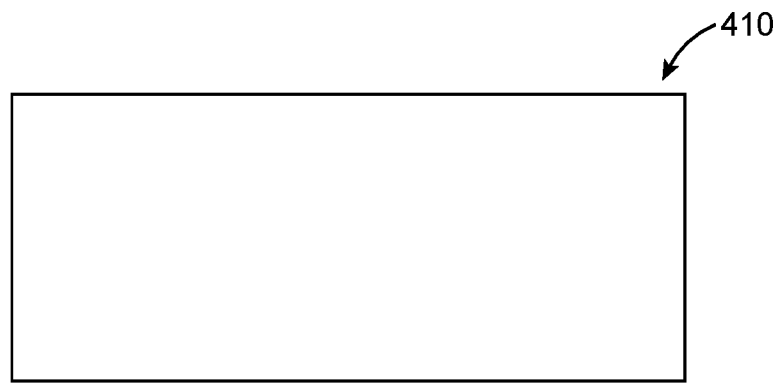
FIG. 9A shows a top view of an energy delivery apparatus consistent with embodiments shown in FIGS. 2B, 2F, 2G, and 2H.
Figure 9B:
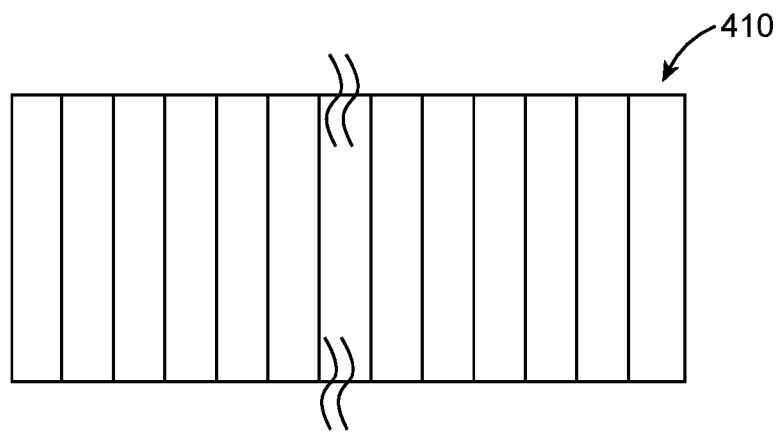
FIG. 9B shows a top view of an energy delivery apparatus composed of a one dimensional array of elements consistent with embodiments shown in FIGS. 2B, 2F, 2G, and 2H.
Figure 9C:
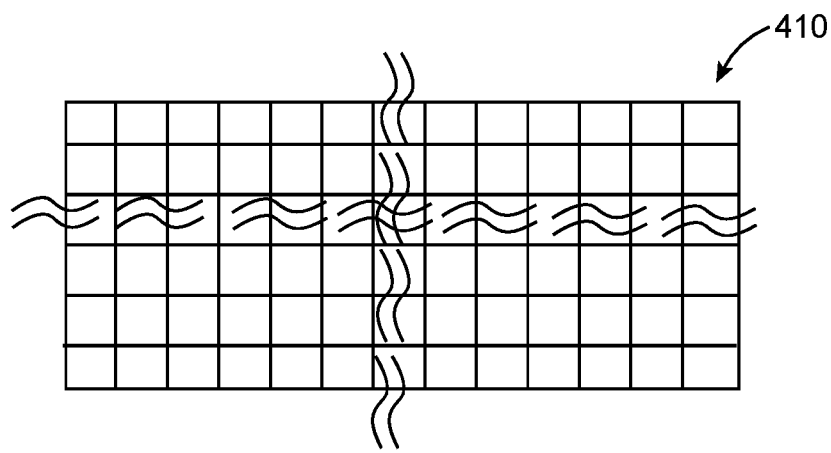
FIG. 9C shows a top view of an energy delivery apparatus composed of a two dimensional array of elements consistent with embodiments shown in FIGS. 2B, 2F, 2G, and 2H.

FIG. 9A shows a top view of an energy delivery apparatus consistent with embodiments shown in FIGS. 2B, 2F, 2G, and 2H. Square or rectangular element dimensions are suited for energy directed from along the longitudinal dimension of the housing 480. This single element may deliver energy for therapy and energy for imaging by temporally interleaving electrical excitations of the element. Duty cycles defined by the duration of therapy divided by the duration of therapy and imaging are typically greater than 50%, and preferably above 75% as to maintain a sufficiently high rate of energy to heat the tissue to irreversible damage. Preferred duty cycle rates depend on the selected acoustic intensity as higher duty cycles may be required for lower acoustic intensities.

FIG. 9B shows a top view of an energy delivery apparatus composed of a one dimensional array of elements consistent with embodiments shown in FIGS. 2B, 2F, 2G, and 2H. Elements contained within may share therapy and imaging actions per temporally interleaved excitations, or particular elements may be dedicated for either therapy or imaging. The advantage of using multiple elements is two-fold and is made possible by the use of electronic steering; acoustic beam forming with acoustic transducer elements. Imaging beams may be focused and steered in preferred directions to optimize spatial resolution and the reach of the field of view of the imaging plane. Therapy beams may be specifically defocused to preserve a substantially collimated beam for distance independent lesion formation.

FIG. 9C shows a top view of an energy delivery apparatus composed of a two dimensional array of elements consistent with embodiments shown in FIGS. 2B, 2F, 2G, and 2H. This array configuration as the same advantages as discussed in FIG. 9B with the additional advantage that steering, focusing, and defocusing may be accomplished in more than a single plane.

Figure 10A:
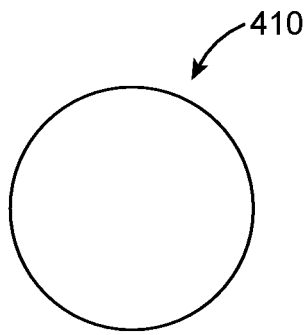
FIG. 10A shows a top view of an energy delivery apparatus consistent with embodiments shown in FIGS. 2A, 2C, 2D, 2E, 2G, and 2H.

FIG. 10A shows a top view of an energy delivery apparatus consistent with embodiments shown in FIGS. 2A, 2C, 2D, 2E, 2G, and 2H. This single element may deliver energy for therapy and energy for imaging by temporally interleaving electrical excitations of the element. Duty cycles defined by the duration of therapy divided by the duration of therapy and imaging are typically greater than 50%, and preferably above 75% as to maintain a sufficiently high rate of energy to heat the tissue to irreversible damage. Preferred duty cycle rates depend on the selected acoustic intensity as higher duty cycles may be required for lower acoustic intensities.

Figure 10B:
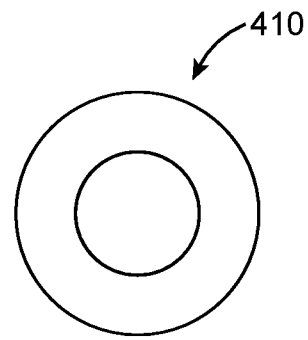
FIG. 10B shows a top view of an energy delivery apparatus composed of a one dimensional radial array of elements consistent with embodiments shown in FIGS. 2A, 2C, 2D, 2E, 2G, and 2H.

FIG. 10B shows a top view of an energy delivery apparatus composed of a one dimensional radial array of elements consistent with embodiments shown in FIGS. 2A, 2C, 2D, 2E, 2G, and 2H. More than two elements may be used although not shown here. Elements contained within may share therapy and imaging actions per temporally interleaved excitations, or particular elements may be dedicated for either therapy or imaging. The advantage of using multiple elements is two-fold. Imaging beams may be focused and steered along the axis of the main beam to optimize spatial resolution. Therapy beams may be specifically defocused to preserve a substantially collimated beam for distance independent lesion formation.

Figure 10C:
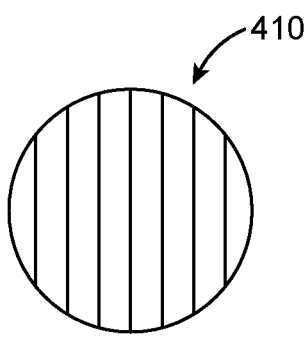
FIG. 10C shows a top view of an energy delivery apparatus composed of a one dimensional array of elements consistent with embodiments shown in FIGS. 2A, 2C, 2D, 2E, 2G, and 2H.

FIG. 10C shows a top view of an energy delivery apparatus composed of a one dimensional array of elements consistent with embodiments shown in FIGS. 2A, 2C, 2D, 2E, 2G, and 2H. Elements contained within may share therapy and imaging actions per temporally interleaved excitations, or particular elements may be dedicated for either therapy or imaging. The advantage of using multiple elements is two-fold. Imaging beams may be focused and steered in preferred directions to optimize spatial resolution. Therapy beams may be specifically defocused to preserve a substantially collimated beam for distance independent lesion formation.

Figure 10D:
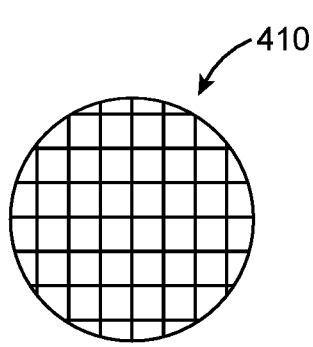
FIG. 10D shows a top view of an energy delivery apparatus composed of a two dimensional array of elements consistent with embodiments shown in FIGS. 2A, 2C, 2D, 2E, 2G, and 2H.

FIG. 10D shows a top view of an energy delivery apparatus composed of a two dimensional array of elements consistent with embodiments shown in FIGS. 2A, 2C, 2D, 2E, 2G, and 2H. This array configuration as the same advantages as discussed in FIG. 10D with the additional advantage that steering, focusing, and defocusing may be accomplished in more than a single plane.

Figure 10E:
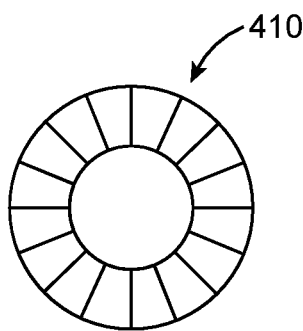
FIG. 10E shows a top view of an energy delivery apparatus composed of a two dimensional array of elements consistent with embodiments shown in FIGS. 2A, 2C, 2D, 2E, 2G, and 2H.

FIG. 10E shows a top view of an energy delivery apparatus composed of a two dimensional array of elements consistent with embodiments shown in FIGS. 2A, 2C, 2D, 2E, 2G, and 2H. This array configuration is a further example of how a two dimensional array may be configured in one of many patterns.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for creating necrosis of a tissue in a wall of an artery, said system comprising:
   a catheter comprising an ultrasound transducer disposed at a distal end of the catheter, the ultrasound transducer being configured to both generate and deliver:
      (i) a collimated therapy beam of ultrasound energy that is sufficient to cause necrosis of the tissue with the distal end of the catheter disposed a distance away from the wall of the artery; and
      (ii) an imaging beam of ultrasound energy suitable for imaging the wall of the artery without creating damage to the tissue; and
   a controller operably coupled to the ultrasound transducer and configured to:
      translate and rotate the ultrasound transducer while delivering the collimated therapy beam of ultrasound energy with the distal end of the catheter and the ultrasound transducer disposed within the artery and avoiding contact with the wall of the artery;
      determine a thickness of the wall of the artery based at least in part on reflected ultrasound energy detected by the ultrasound transducer; and
      adjust energy parameters or movement of the ultrasound transducer in response to the determined thickness of the wall of the artery.

2. The system of claim 1, wherein the ultrasound transducer is configured to deliver the collimated therapy beam and the imaging beam from the distal end of the catheter in a generally radial direction with respect to an axis of the distal end of the catheter.

3. The system of claim 1, further comprising a cooling apparatus for cooling the ultrasound transducer.

4. The system of claim 1, further comprising an energy delivery apparatus, wherein the ultrasound transducer is at least partially recessed within the energy delivery apparatus.

5. The system of claim 1, wherein the catheter comprises one or more deflectable regions, the one or more deflectable regions being deflectable in at least one direction.

6. The system of claim 1, wherein the controller is configured to direct movement of the catheter in a helical pattern along the wall of the artery to produce a helical lesion in the wall of the artery.

7. The system of claim 1, wherein the controller is further configured to direct movement of the catheter to produce a spotted lesion pattern in the wall of the artery.

8. The system of claim 1, wherein the controller is further configured to direct movement of the catheter to produce an intermittent spiral lesion pattern in the wall of the artery.

9. The system of claim 1, wherein the controller is configured to deliver pain reduction medication to the wall of the artery using the catheter.

10. The system of claim 9, wherein the controller is further configured to activate the pain reduction medication through at least one of ultrasound stimulation or thermal stimulation.

11. The system of claim 1, further comprising a pain reduction medication delivery tube associated with the distal end of the catheter.

12. The system of claim 1, wherein the distance that the distal end of the catheter is disposed away from the wall of the artery allows for blood flow and fluid provided from the catheter between the distal end of the catheter and the wall of the artery to remove heat from the wall of the artery.

13. The system of claim 1, further comprising a fluid path in the catheter for delivering a pain reduction medicament.

14. The system of claim 1, wherein the distance that the distal end of the catheter is disposed away from the wall of the artery prevents damage to the wall of the artery from abrasion and reduces thermal conductivity from the distal end of the catheter to the wall of the artery.

15. The system of claim 1, wherein the artery is a renal artery and wherein necrosis of the tissue comprises necrosis of a nerve.

16. The system of claim 15, wherein the necrosis of the nerve alleviates hypertension in a patient.

17. The system of claim 1, further comprising an irrigation fluid flowing through the catheter.

18. The system of claim 17, wherein the irrigation fluid reduces heat and damage to the tissue on an intima of the wall of the artery.

19. The system of claim 18, wherein the necrosis is greater within the wall of the artery relative to the intima of the wall of the artery.

\* \* \* \* \*